(12) United States Patent
Noble

(10) Patent No.: US 6,637,434 B2
(45) Date of Patent: Oct. 28, 2003

(54) NASAL GAS DELIVERY SYSTEM AND METHOD FOR USE THEREOF

(75) Inventor: James Noble, Stuart, FL (US)

(73) Assignee: Linda J. Noble, Stuart, FL (US)

( * ) Notice: Subject to any disclaimer, the term of this patent is extended or adjusted under 35 U.S.C. 154(b) by 0 days.

(21) Appl. No.: 10/183,498

(22) Filed: Jun. 28, 2002

(65) Prior Publication Data

US 2002/0162558 A1 Nov. 7, 2002

Related U.S. Application Data

(63) Continuation-in-part of application No. 09/430,038, filed on Oct. 29, 1999.
(60) Provisional application No. 60/106,271, filed on Oct. 30, 1998.

(51) Int. Cl.[7] .......................... A61M 15/08; A62B 7/00
(52) U.S. Cl. ................................... 128/207.18
(58) Field of Search ................. 128/202.24, 203.22, 128/204.12, 207.13, 207.18, DIG. 26, 912

(56) References Cited

U.S. PATENT DOCUMENTS

| | | | |
|---|---|---|---|
| 1,155,608 A | | 10/1915 | Nieschang |
| 2,672,138 A | * | 3/1954 | Carlock ................. 128/207.18 |
| 4,648,398 A | | 3/1987 | Agdanowski et al. |
| 4,660,555 A | | 4/1987 | Payton |
| 4,676,241 A | | 6/1987 | Webb et al. |
| 4,742,824 A | | 5/1988 | Payton et al. |
| 4,753,233 A | | 6/1988 | Grimes |
| 4,782,832 A | | 11/1988 | Trimble et al. |
| 4,915,104 A | | 4/1990 | Marcy |
| 4,915,105 A | | 4/1990 | Lee |
| 4,996,983 A | | 3/1991 | AmRhein |
| 5,062,420 A | | 11/1991 | Levine |
| 5,113,857 A | | 5/1992 | Dickerman et al. |
| 5,117,818 A | | 6/1992 | Palfy |
| 5,134,995 A | | 8/1992 | Gruenke et al. |
| 5,188,101 A | | 2/1993 | Tumolo |
| 5,222,486 A | | 6/1993 | Vaughn |
| 5,267,556 A | | 12/1993 | Feng |
| 5,269,296 A | | 12/1993 | Landis |
| 5,284,134 A | | 2/1994 | Vaughn et al. |
| 5,333,608 A | | 8/1994 | Cummins |
| 5,335,659 A | * | 8/1994 | Pologe .................. 128/207.18 |
| 5,507,535 A | | 4/1996 | McKamey et al. |
| 5,533,506 A | | 7/1996 | Wood |
| 5,535,739 A | | 7/1996 | Rapoport et al. |
| 5,595,174 A | | 1/1997 | Gwaltney |

(List continued on next page.)

Primary Examiner—Weilun Lo
Assistant Examiner—Joseph F. Weiss, Jr.
(74) Attorney, Agent, or Firm—Wenderoth, Lind & Ponack, L.L.P.

(57) ABSTRACT

A gas administering method for administering gas to an airway of a patient having a nasal vestibule and for use with a gas administering apparatus comprises a primary gas source that is operable to provide gas and a nasal vestibular portion arranged so as to receive the gas from the primary gas source. Further, the nasal vestibular portion is capable of releasing the primary gas into the nasal vestibule. The method comprises inserting the nasal vestibular portion into the nasal vestibule, forming a seal between the nasal vestibular portion and an inner surface of the nasal vestibule, administering an amount of a gas from the primary gas source at a constant flow rate into the nasal vestibule via the nasal vestibular portion, and administering an anesthetic to the patient. The anesthetic induces depression of a portion of the nervous system of the patient. Furthermore, the seal promotes airway pressure buildup that is sufficient to prevent obstruction of the airway during depression of at least a portion of the nervous system and prevents escape of the gas from between the nasal vestibule and the nasal vestibular portion.

44 Claims, 8 Drawing Sheets

U.S. PATENT DOCUMENTS

| | | |
|---|---|---|
| 5,715,813 A | 2/1998 | Guevrekian |
| 5,775,335 A | 7/1998 | Seal |
| 5,794,619 A * | 8/1998 | Edelman et al. ....... 128/207.18 |
| 6,076,520 A | 6/2000 | Cooper |
| 6,119,694 A | 9/2000 | Correa et al. |
| 6,123,072 A | 9/2000 | Downs |
| 6,263,874 B1 | 7/2001 | LeDez et al. |
| 6,379,312 B2 | 4/2002 | O'Toole |
| 6,439,234 B1 * | 8/2002 | Curti et al. ............. 128/207.18 |
| 6,561,193 B1 * | 5/2003 | Noble ................... 128/207.18 |

* cited by examiner

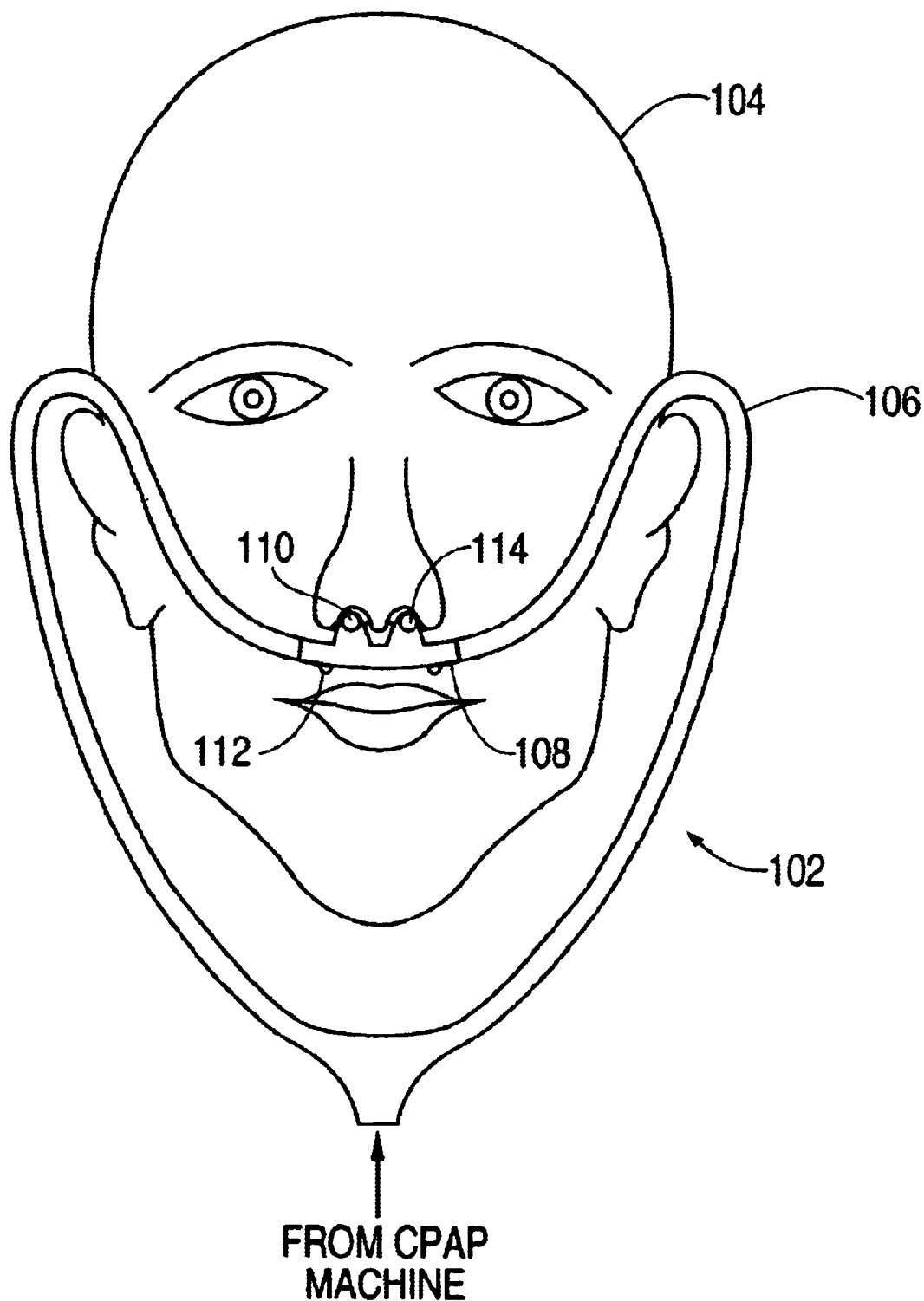

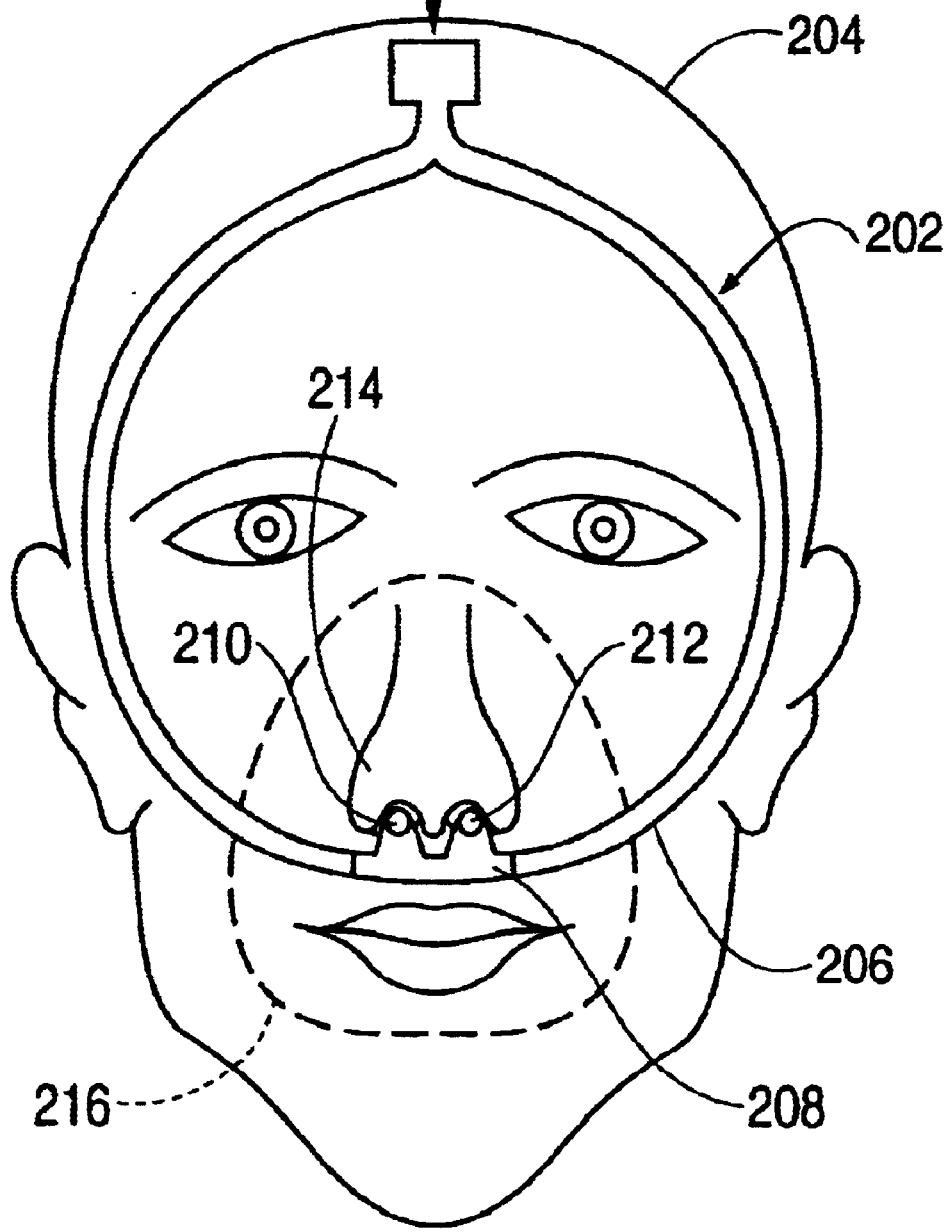

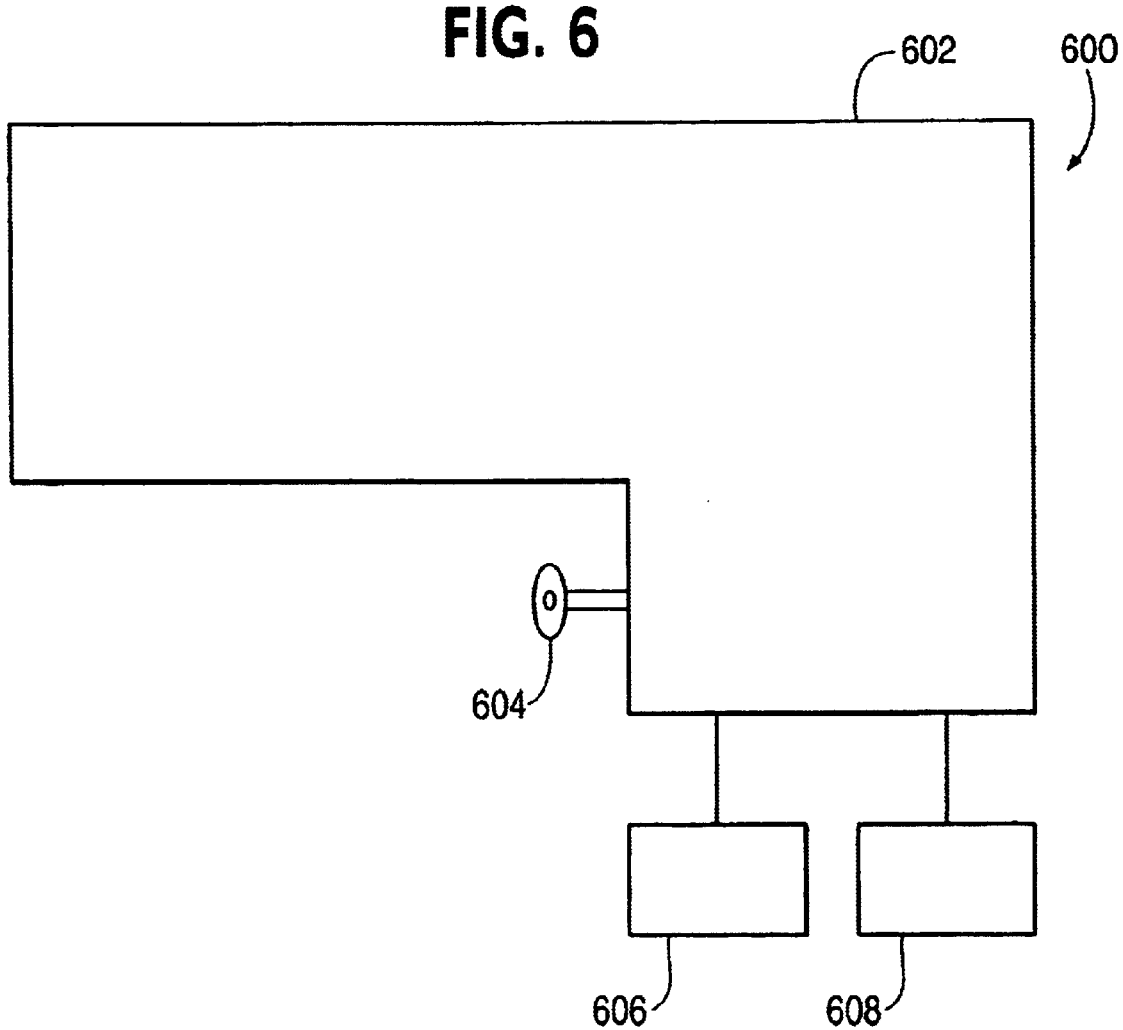

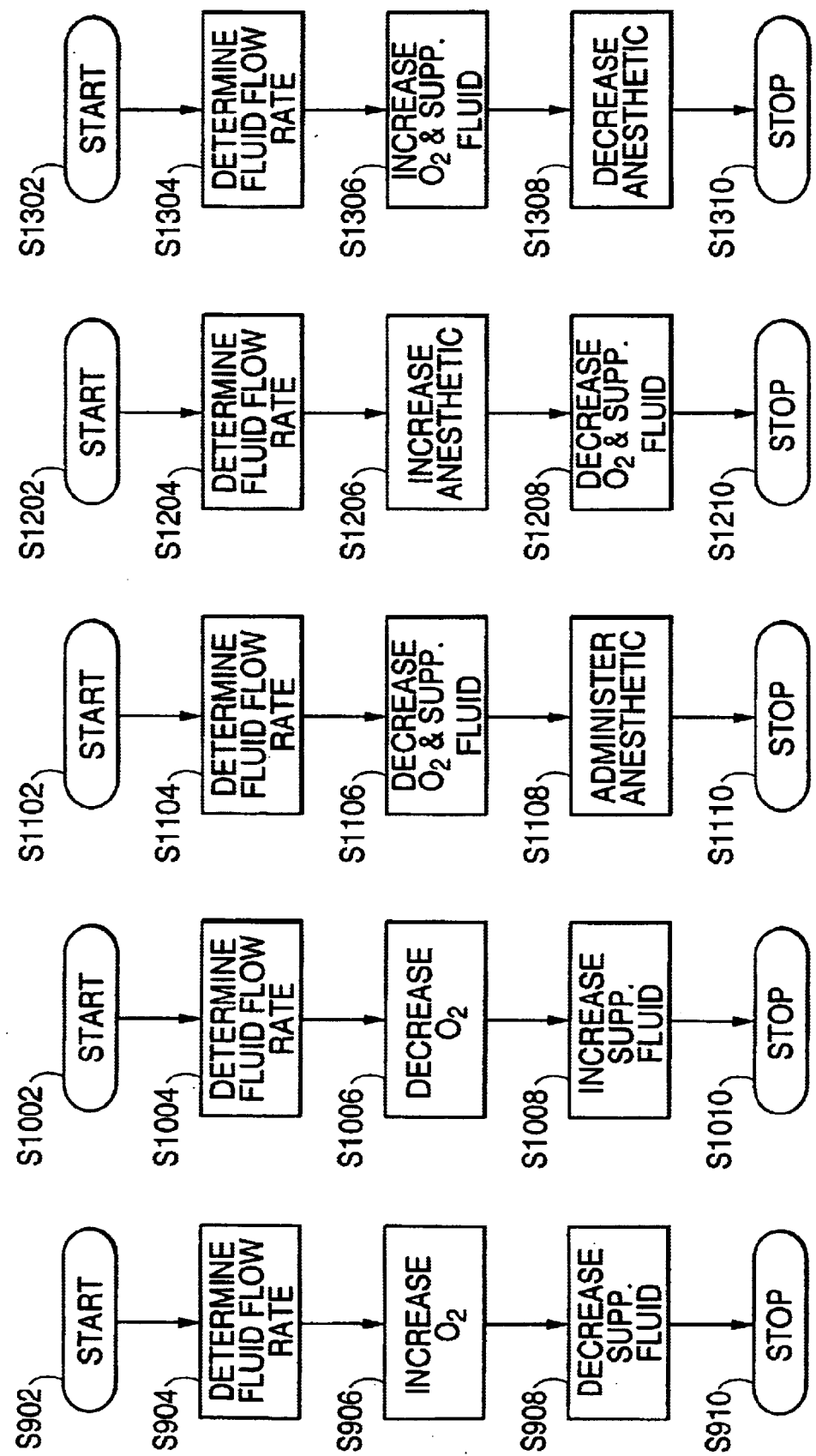
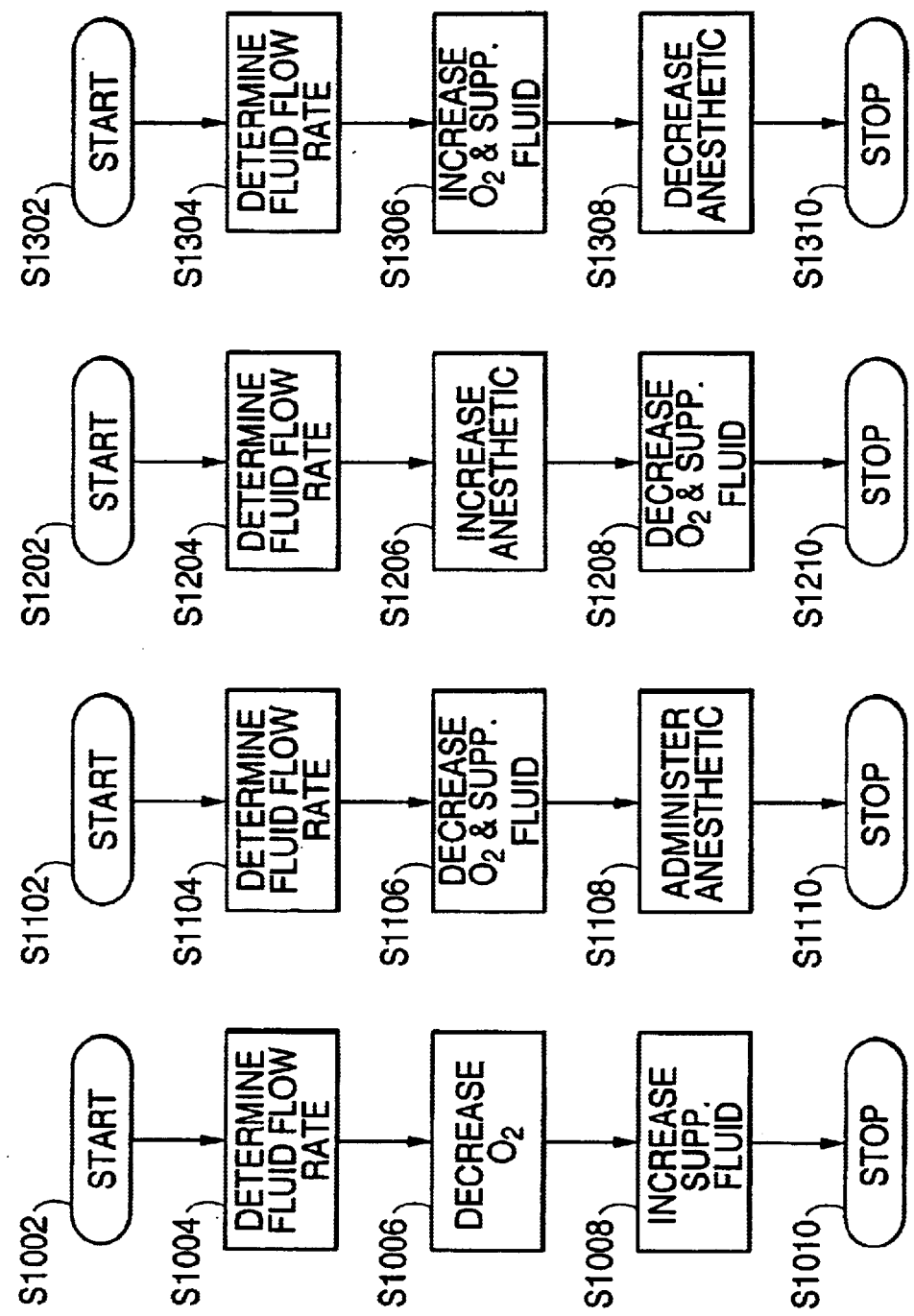
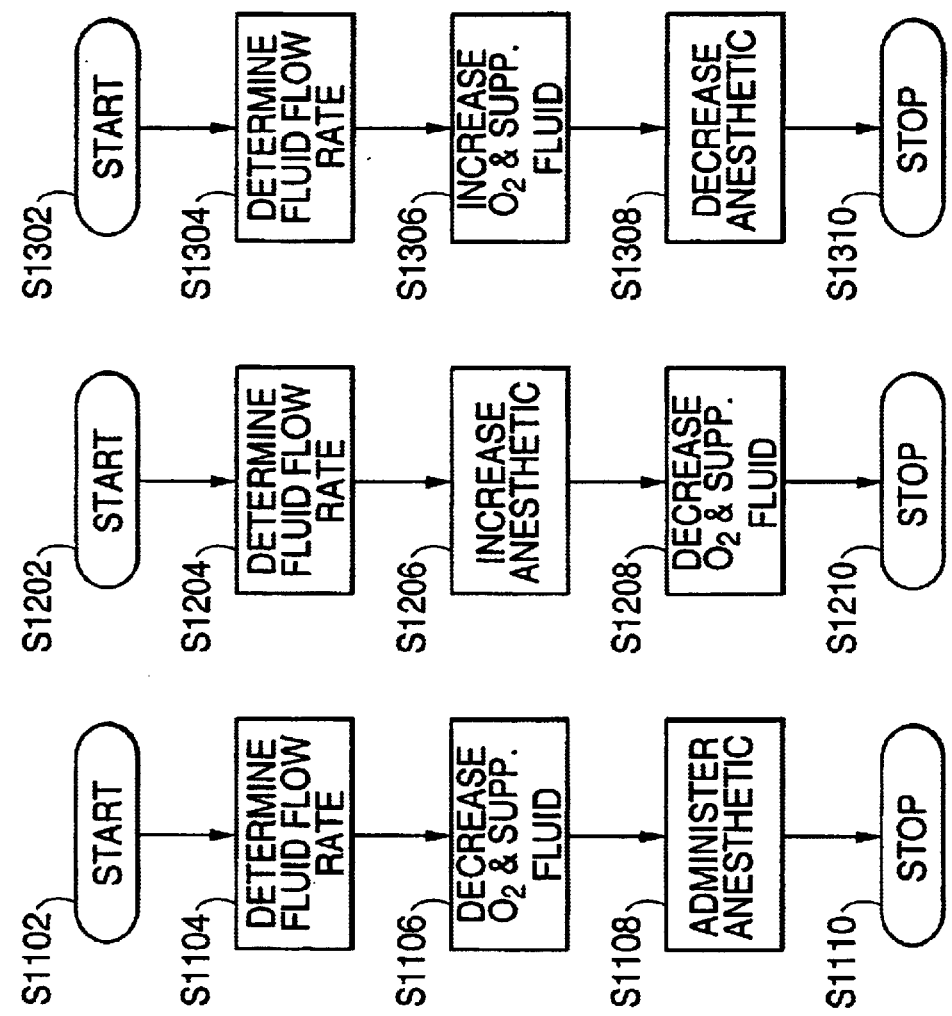
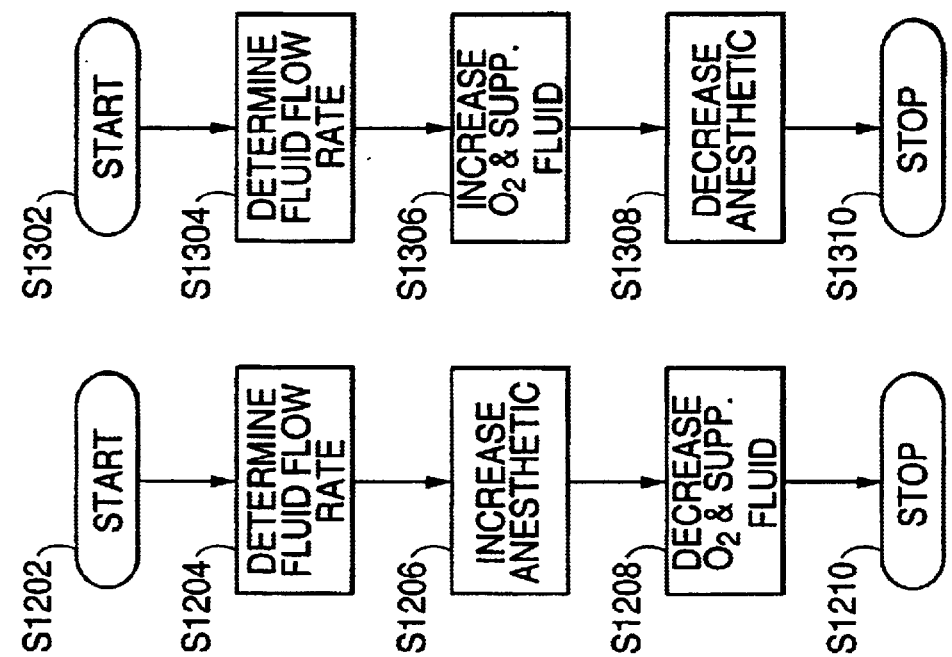
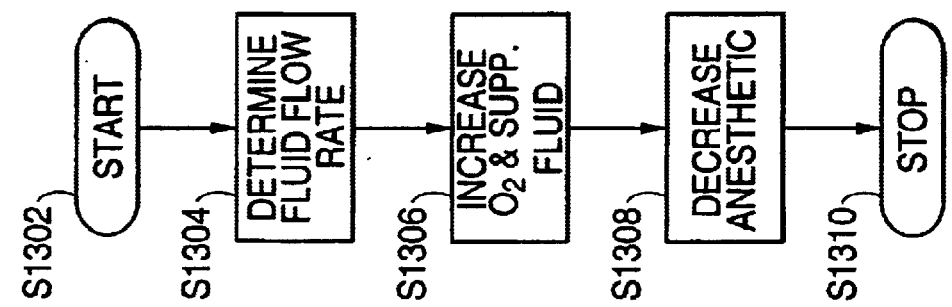

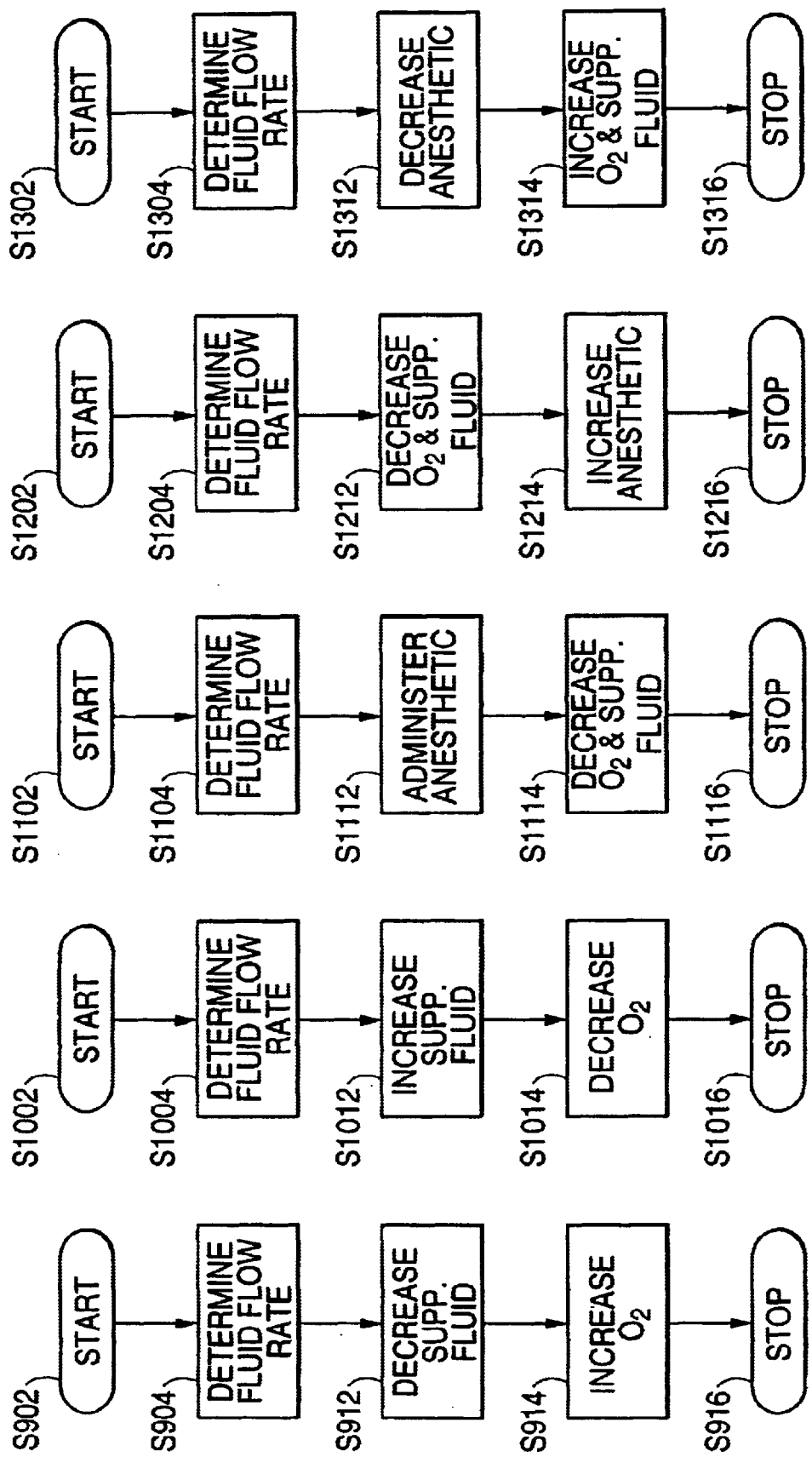
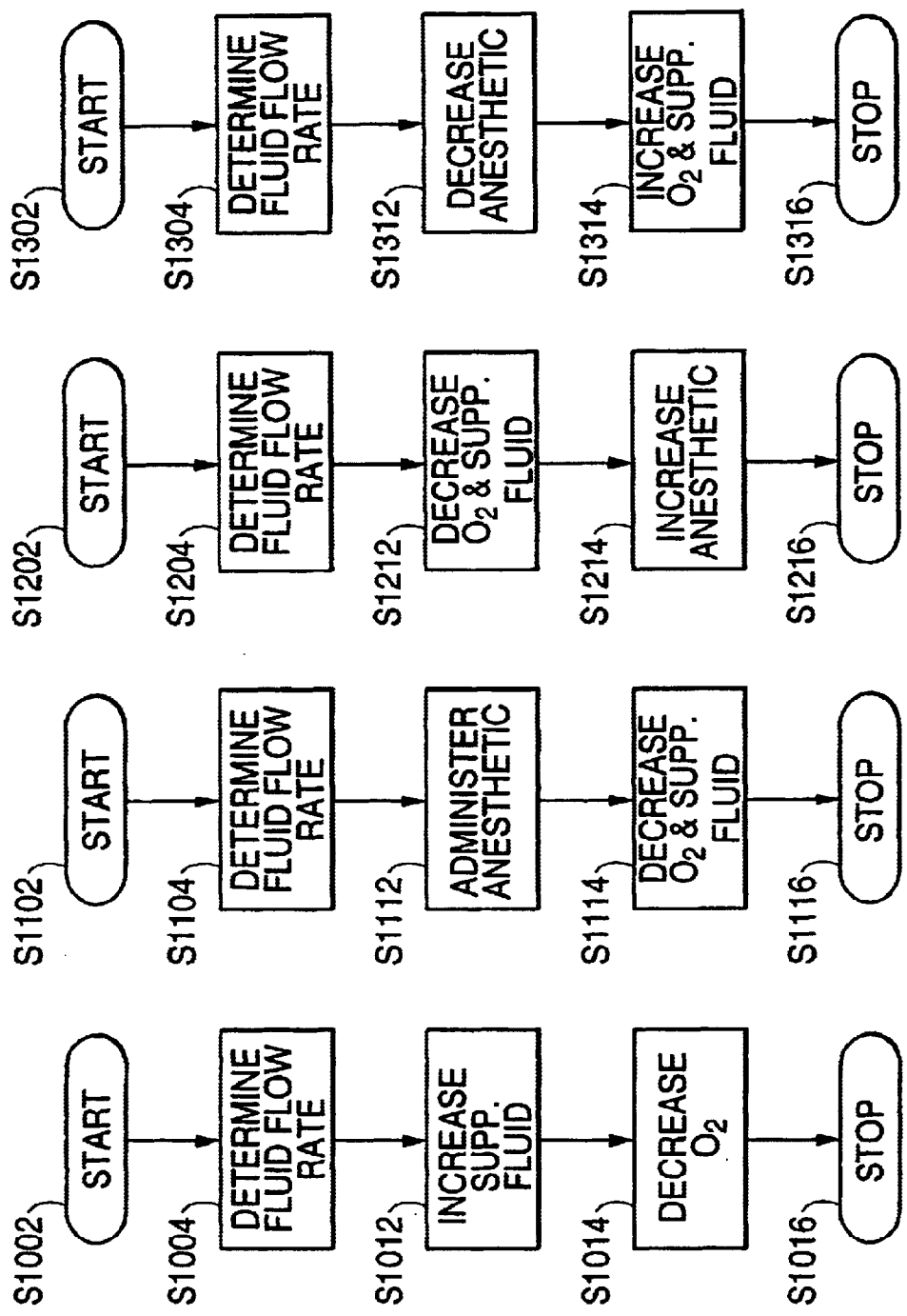
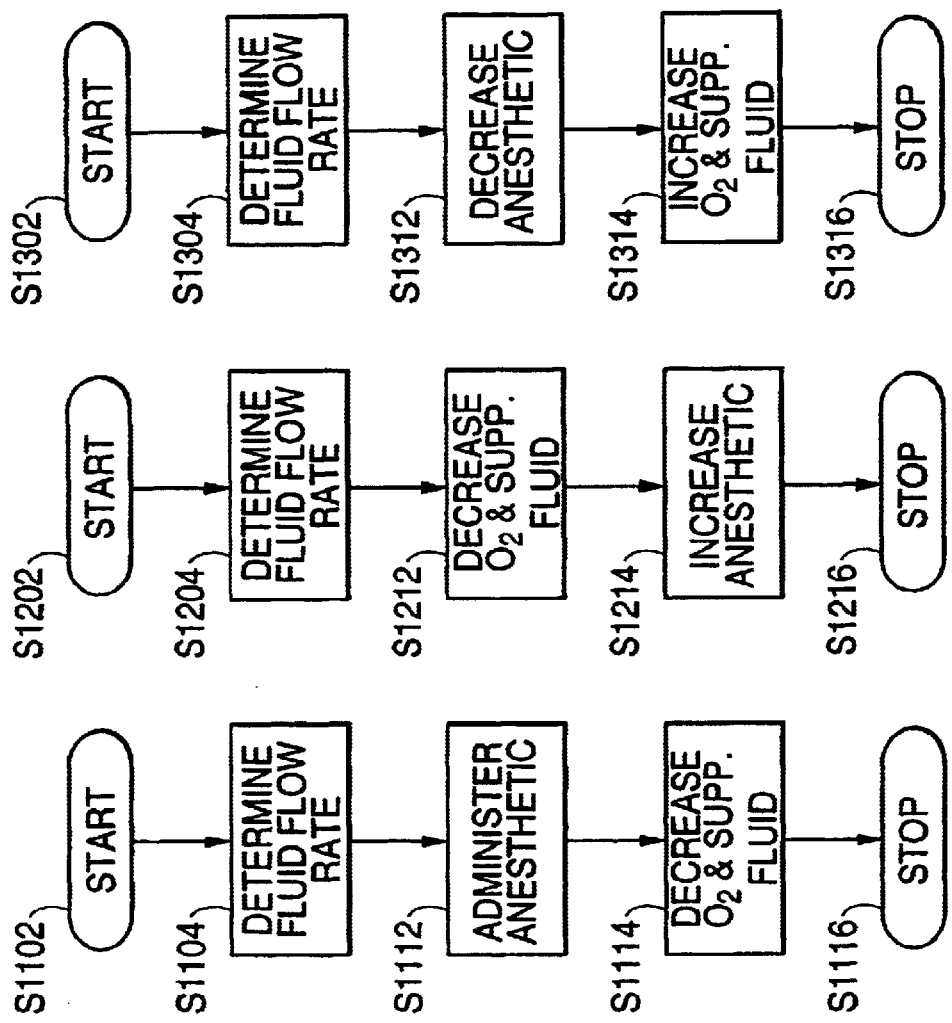
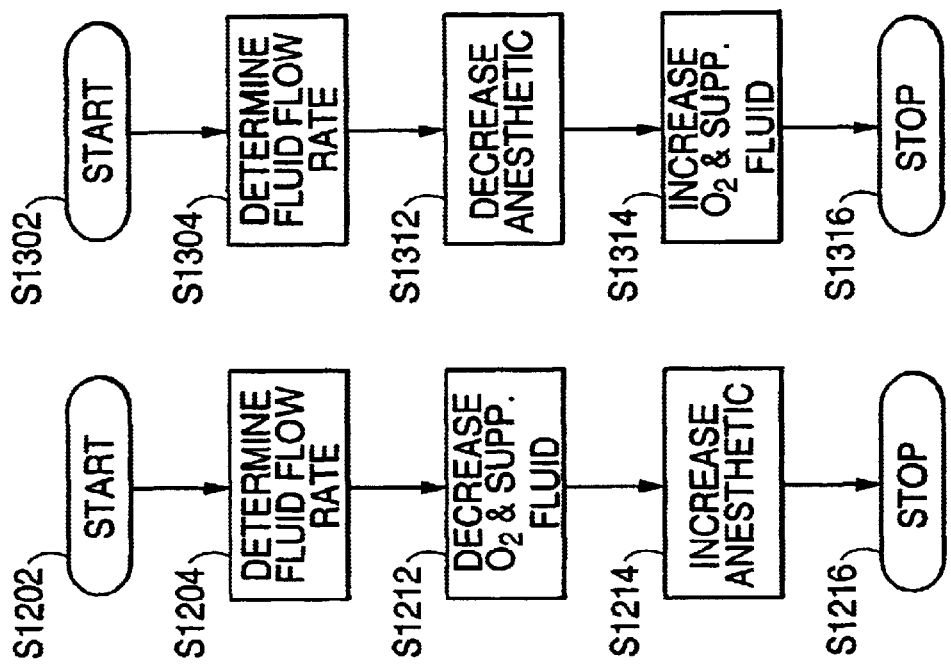
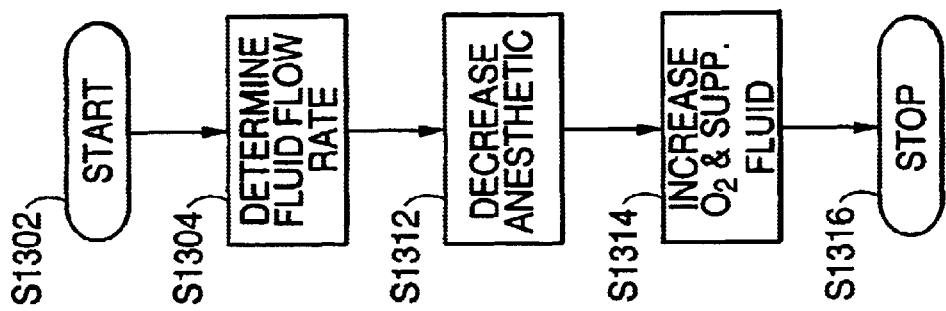

NASAL GAS DELIVERY SYSTEM AND METHOD FOR USE THEREOF

This is a continuation-in-part application of utility application having Ser. No. 09/430,038, filed Oct. 29, 1999, which claims priority on Provisional Application No. 60/106,271, filed Oct. 30, 1998. The entire disclosures of application Ser. Nos. 09/430,038 and 60/106,271 are incorporated herein by reference.

BACKGROUND OF THE INVENTION

The present invention relates to a gas delivery apparatus for administering a gas to a patient during surgery, and more particularly for delivering anesthetic to a patient during surgery During surgical procedures, there is a need to anesthetize a patient in order to eliminate, or at least reduce: pain associated with the procedure; and movement of the patient during the procedure. Anesthesia is considered a drug-induced depression of at least a portion of nervous system, or portion thereof, of the patient.

In the sequence of events of drug-induced depression of the central nervous system, there occurs a level of depression that allows the muscles of the pharynx (e.g. the tongue) to relax causing soft-tissue structures to collapse into and obstruct the airway. This happens at an earlier stage than that at which the muscles of respiration (e g the diaphragm) cease to function. In other words, a condition known as "obstructive apnea," where the diaphragm is struggling to pull air through an obstruction of the upper airway occurs before the diaphragm itself ceases to function ("central apnea"). In this sequential depression of the central nervous system, death occurs from Asphyxia before the drug itself can produce complete depression of the nervous system.

An upper airway obstruction occurs upon the induction of almost every general anesthetic and is a frequent occurrence during the administration of heavy sedation for procedures done nominally under "local anesthesia with sedation." Under most conditions, the treatment is so routine as to be taken for granted by practitioners skilled in airway management. Manual support of the airway such as with an invasive endotracheal tube, application of a face mask over the mouth and nose and various other airway devices are employed, often with supplemental oxygen.

However, the use of a face mask or an endotracheal tube during surgical procedures has many drawbacks. The standard face mask places pressure on the chin and tends to collapse soft-tissue structures of the oropharynx. Additionally, air pressure that is applied through the face mask tends to equalize through the nose and the mouth, and therefore it can be counter-productive to the supporting of soft tissue to open the airway. Further, using a face mask usually requires one or two additional maneuvers, for example manual support of the chin, the insertion of an oral airway, etc., in order to remedy the problem. None of the invasive airway-support devices currently used in conventional anesthesia practice can be inserted in the conscious patient without causing significant discomfort and/or physiological disturbance.

Furthermore, recent advances in cosmetic surgery have made airway management significantly more challenging and have caused practitioners to accept conditions having a reduced margin of safety for their patients. In particular, laser procedures on the face are requiring heavier sedation leading more often to respiratory depression and obstruction while, at the same time, the increased fire hazard restricts the use of oxygen.

Obstructive Sleep Apnea (OSA), a syndrome defined in the early 1980's, is similar to drug-induced obstructive apnea in anatomy and treatment. The treatment of OSA has demonstrated that upper airway obstruction occurring during the sleep of afflicted patients can be relieved by the application of positive pressure through the nose alone. OSA differs from drug-induced obstructive apnea in that it is not drug-induced. Further, OSA typically does not have acutely disastrous consequences, but rather has long-term ill-effects and is a chronic condition.

A conventional method for treating a form of OSA is to provide a continuous positive airway pressure (C-PAP) through the nose in order to prevent an upper airway obstruction. Nasal masks are used, as are nasal insert devices. InnoMed Technologies, for instance, provides a device called NasalAire used to treat obstructive sleep apnea. The device includes conical shaped nasal inserts connected to gas delivery tubes which are connected to an air delivery system. A C-PAP generator is included, which automatically increases and decreases air flow rate to maintain a continues positive airway pressure. Furthermore, the device includes vent holes for venting $CO_2$ from the exhaling user.

FIG. 1 illustrates a conventional system for treating sleep induced apnea by providing a continuous positive airway pressure through the nose. As depicted in the figure, the patient 104 is fitted with tubing 102. The tubing 102 receives airflow from a C-PAP machine and administers the airflow to the nose of the patient by tube branches 106. An airflow delivery device 108, having nasal inserts 110 is placed such that nasal inserts 110 are disposed within the nasal vestibules 114 of patient 104. Airflow delivery device 108 additionally includes ventilation holes 112, which provide ventilation for $CO_2$ from the user during expiration. Examples of such devices are disclosed in U.S. Pat. No. 5,533,506 to Wood, U.S. Pat. No. 4,702,832 to Tremble et al, and U.S. Pat. No. 5,134,995 to Gruenke et al., the entire disclosures of which are incorporated herein by reference.

What is needed is a method and apparatus for preventing complete airway obstruction of a patient when the patient is deeply sedated after induction of anesthesia.

What is additionally needed is a method and apparatus for enabling a patient to adequately respire at surgical levels of anesthesia without an invasive airway and manual or mechanized ventilation.

What is additionally needed is a method and apparatus for cost-effectively adding air to the anesthetic gasses for reducing the risk of combustion in the surgical field when using cautery or laser devices.

What is additionally needed is a method and apparatus for preventing leakage of the anesthesia to the operating room.

What is additionally needed is a method and apparatus for more accurately monitoring spontaneous respirations in a pressurized system.

What is additionally needed is a method and apparatus for preventing an airflow generator from excessively pressurizing an anesthesia circuit.

What is additionally needed is an apparatus that is: operably connectable to an existing anesthetic delivery apparatus; operable to prevent complete airway obstruction of a patient when the patient is deeply sedated after induction of anesthesia; and operable to enable a patient to adequately respire at surgical levels of anesthesia without an invasive airway and manual or mechanized ventilation.

SUMMARY OF THE INVENTION

It is the object of this invention to provide a method and apparatus that may comfortably be applied to the conscious patient prior to the induction of anesthesia to prevent airway obstruction and maintain oxygenation after the patient has become unconscious under the influence of anesthesia.

It is another object of this invention to enable a patient to adequately respire at surgical levels of anesthesia without an invasive airway and manual or mechanized ventilation.

It is another object of this invention to cost-effectively add air to the anesthetic gasses for reducing the risk of combustion in the surgical field when using cautery or laser devices.

It is another object of this invention to prevent leakage of the anesthesia to the operating room.

It is another object of this invention to more accurately monitor spontaneous respirations in a pressurized system.

It is another object of this invention to prevent an airflow generator from excessively pressurizing an anesthesia circuit.

Upper airway obstruction caused by a drug-induced depression of the central nervous system is preventable by applying positive pressure through the nasopharynx while leaving the oral cavity open to ambient pressure. The pressure differential thus created, splints the soft tissues out of the airway with a natural pressure relief valve through the oral cavity. The maximum pressure obtainable is consistently sufficient to relieve the obstruction, but is less than the 20 centimeters of water that might send air to the stomach.

In accordance with one method of the present invention, nasal oxygen is applied to an awake patient through a sealed nasal connection. A conventional anesthesia administering apparatus, i.e., anesthesia circuit, that is unable to provide air to a patient may be modified to include an air supply. In any event, a conventional anesthesia administering apparatus can be modified in accordance with the present invention to provide a sealed nasal connection. Nasal oxygen may be applied as 100% oxygen, or a diluted form of oxygen by supplying air.

The sealed nasal connection may be provided by any device that may: be inserted into the nasal vestibule of the patient; provide a seal between the device and an inner surface of the nasal vestibule; and administer an amount of a gas into the nasal vestibule via the nasal vestibular portion, wherein the seal promotes airway pressure buildup that is sufficient to prevent obstruction of the airway during depression of at least a portion of the nervous system and prevents escape of the gas from between the nasal vestibule and the device. For example, the sealed nasal connection may be provided by a device having a nasal vestibular portion that is shaped as portions of the devices as disclosed in U.S. Pat. No. 5,533,506 to Wood, U.S. Pat. No. 4,702,832 to Tremble et al, U.S. Pat. No. 5,134,995 to Gruenke et al., U.S. patent application Ser. No. 09/430,038, the entire disclosures of which are incorporated herein by reference.

Unlike the airflow delivery device 108 discussed above with reference to FIG. 1, the sealed nasal connection of the present invention cannot include ventilation holes. In particular, the ventilation holes 112 of airflow delivery device 108 provide ventilation for $CO_2$ of the user during expiration. However, such vent holes would be counter-productive if included in the sealed nasal connection of the present invention. In particular, such vent holes would enable gas, that would otherwise have been forced into the airway of the patient to prevent airway obstruction, to escape. Accordingly, the ability for the sealed nasal connection of the present invention to prevent airway obstruction would be reduced.

Once nasal oxygen is administered to the awake patient, the patient is forced to breathe in through the nose and out through the mouth. The patient will do so fairly comfortably as long as the nasal oxygen flow rate is adjusted to comfort.

Anesthesia is then induced, either intravenously or inhalationally through the sealed nasal connection. Then, when anesthesia is induced and total relaxation of the pharyngeal muscles occurs, obstruction is prevented automatically as pressure within the anesthetic circuit builds to prop open the patient's airway. With the mouth left open to ambient pressure in the deeply sedated patient, a pressure gradient is established which allows the soft palate and tongue to be propped out of the pharyngeal airway while at the same time creating a low pressure seal of the soft palate to the tongue which remarkably releases somewhat between 8 and 20 cm of water pressure. There is, in effect, a pressure "pop-off" valve that prevents a pressure build-up which would force air into the stomach (20 cm of water is the reported threshold pressure).

Aspiration of gastric acid into the lungs may result in fatal pneumonitis, which is the classic nightmare of anesthesia practice. Over-inflation of the lungs with pharyngeal pressures in excess of 20 cm of water has been shown to blow air into the stomach. The resultant distension of the stomach with air under pressure has been known to cause regurgitation and subsequent aspiration of acid into the lungs. However, C-PAP under 20 cm of water has been shown to oppose the reflux of acid up the esophagus by increasing the intra-thoracic pressure above the intra-abdominal pressure. This serves to create a pressure gradient which opposes reflux under anesthesia.

The reflex apnea triggered by obstruction is prevented and the patient resumes spontaneous respirations after a few seconds of central apnea, which may occur as a consequence to the direct depression of the central nervous system by the anesthetic drug itself.

Deep levels of inhalational anesthesia can be achieved through spontaneous and unassisted respirations. Then, with the sealed nasal connection left in place, anesthesia and oxygenation can be sustained during, for example, a difficult intubation where ordinarily the removal of the oxygen mask would effectively remove adequate oxygenation from the patient. In theory, as long as 100% oxygen is provided at the level of the open vocal chords, even a patient who is not breathing will remain well-oxygenated and viable for nearly an hour. In particular, the patient will maintain adequate ventilation spontaneously when connected to the closed anesthesia circuit with the nasal oxygen flow rate adjusted to maintain a positive pressure sufficient to prevent obstruction. In other words, the patient is enabled to respire adequately, at surgical levels of anesthesia, totally free of an invasive airway and manual or mechanized ventilation.

In accordance with a method of the present invention, a more strict monitoring method is required to detect early partial airway obstruction. For example, a more sensitive anesthetic circuit pressure gauge and a supra-sternal stethoscope may be used. In particular, a conventional pressure gauge in a conventional anesthesia circuit is scaled to approximately 160 units over the full circumference of its face (1 unit=1 centimeter of water pressure). On the contrary, a pressure gauge in accordance with the present invention would be more sensitive and have a scale of 40 units over the same circumference. The fluctuations of the needle of the gauge would, therefore, be amplified by a factor of four making it a sensitive monitor of the alternating pressures of the respiratory cycle. Further, as stated above, because pressures in excess of 20 cm of water has been shown to blow air into the stomach, the pressure gauge must be able to measure at least 20 cm of water. More importantly, the pressure gauge in accordance with the present invention should display the detected pressure at a precision that would readily communicate the difference between a inspiration and an expiration of the patient.

The airway pressure used under anesthesia, in accordance with the present invention, is not C-PAP as applied in the treatment of obstructive sleep apnea. The airflow rate of a C-PAP generator automatically increases and decreases to maintain a constant positive airway pressure. On the contrary, in accordance with the present invention, a gas flow rate to the patient is constant and is manually adjusted to a level that produces a positive pressure, which prevents obstruction. An apparatus in accordance with the present invention is capable of providing a supplemental gas, such as for example oxygen or air, at a constant, adjustable, flow rate to the patient. Using a method in accordance with the present invention, the supplemental gas is supplied in an amount such that there is a constant gas flow rate and there is always a positive pressure, but the magnitude of the pressure varies with respiration. This approach, i.e., using a constant gas flow rate, causes airway pressure to be higher on expiration than on inspiration. The varying pressure and constant gas flow rate provided by the method and apparatus of the present invention is advantageous over conventional C-PAP because the constant gas flow rate and varying pressure promotes a better venous return to the heart. The varying pressure accompanied with the constant gas flow rate in accordance with the present invention is termed alternating positive airway pressure.

The alternating positive airway pressure generated by the system in accordance with the present invention has further beneficial effects. keeps the lungs expanded to a more optimal functional residual capacity, thereby increasing the oxygen reserves within the lungs, which in turn prevents atelectasis from collapse of the alveoli. Further, when air is combined with oxygen, the alternating positive airway pressure generated by the system in accordance with the present invention prevents atelectasis from oxygen absorption. Still further, the alternating positive airway pressure creates a positive intra-thoracic pressure, which serves to reverse any existing tendency towards reflux of gastric contents up the esophagus, which might lead to aspiration into the lungs.

The system and method of use thereof in accordance with the present invention has still further beneficial effects. When inhalational anesthesia is used, the carbon dioxide can be sampled from the scavenger mask to monitor respirations and to assure that the scavenger is working to remove exhaled gas. Depth of anesthesia is rapidly increased by increasing flow rates to the nose so that no exhaled gas comes back into the anesthesia circuit, but rather, is forced out through the mouth. Denitrogenation and oxygenation is facilitated along with the increased flow rate of higher anesthetic gas concentrations into the lungs. Similarly, at the end of the procedure, anesthetic gasses are rapidly eliminated by a unidirectional high flow of oxygen and/or air into the anesthetic circuit. In deep sedation (e.g. MAC, "MONITORED ANESTHESIA CARE"), precise concentrations of oxygen can be monitored and administered to the patient without escaping into the surgical field thereby reducing the fire hazard that accompanies the routine practice of bringing oxygen into the proximity of cautery and laser devices through a standard oxygen cannula.

Many conventional anesthetic delivery machines or facilities do not have the capacity for adding controlled, pressurized air to the anesthetic gasses. More importantly, no conventional anesthetic delivery machines or facilities have the capacity for adding controlled, pressurized air or pure oxygen to the anesthetic gasses such that the total gas flow rate administered to the patient is sufficient to prevent obstruction of the airway during depression of the portion of the nervous system.

A device in accordance with the present invention includes a constant gas flow rate generator that is adaptable for use with a conventional anesthetic delivery machine. The constant gas flow rate generator will add a gas, such as oxygen or air, at a constant gas flow rate of a level that produces a positive pressure that is sufficient to prevent airway obstruction. Furthermore, a constant gas flow rate generator in accordance with the present invention may include an adjustment device, such as an automatic or manual adjustment device, for adjusting the constant gas flow rate. An exemplary embodiment of an automatic adjustment device includes a gas flow rate meter that is operably connected to a gas flow valve. In particular, in operation of the exemplary embodiment of an automatic adjustment device, the gas flow rate may be set by the user. The gas flow rate may be subsequently monitored by the gas flow rate meter, the output of which controls the gas flow valve to open/close in the amounts required to maintain the gas flow rate set by the user. An exemplary embodiment of a manual adjustment device includes a gas flow rate meter that displays a gas flow rate to a user and a gas flow valve. In particular, in operation of the exemplary embodiment of a manual adjustment device, the gas flow rate as displayed by the gas flow rate meter is monitored by the user. The user will then operate the gas flow valve to open/close in the amounts required to maintain the gas flow rate desired by the user.

A gas delivery apparatus according to the present invention includes a nasal insert having a gas passage therein for insertion into the nose, such as for example a device disclosed in U.S. application Ser. No. 09/430,038, which is capable of forming a seal with the inner surface of the nasal vestibule. Bendable tubing is included in the apparatus. The bendable tubing has a proximal portion connected to the nasal vestibular portion so as to be in gas communication with the gas passage of the nasal vestibular portion. The nasal vestibular portion flares outwardly with respect to the gas passage therein.

The nasal vestibular portion may comprise a superior pole for engaging the apex of a nasal vestibule. Further, an inferior pole of the nasal vestibular portion may be provided to engage an inferior nostril rim of the nasal vestibule. The superior pole may be elongated and rounded, and the inferior pole may comprise an angled wedged shape. Thus, the superior pole, lodged in the apex of the nasal vestibule, may be shaped so as to help direct the inferior pole against the inner surfaces of the nose to push the surfaces outward, thereby sealing.

The nasal vestibular portion may comprise a flexible material. In this case, a thin flap can be provided around the perimeter of the nasal vestibular portion for providing further sealing with the nasal interior.

A second nasal vestibular portion may be provided to connect with the second nostril of a patient. The second nasal vestibular portion also flares outwardly with respect to the connection part. A head strap and/or an ear hook may be connected to the tubing to hold the tubing on the head of the patient.

A nasal plug can also be adapted to close one nostril when only one nasal airway is supplied with gas. The nasal plug may be similar to the nasal airway which comprises a connection part and a nasal vestibular portion, but in this case would have its gas passage blocked, for example by a cap. Alternatively, the cap could include a small opening to receive an oxygen tube to provide oxygen to the nostril.

In general, the present invention provides a gas administering method for administering gas to an airway of a patient having a nasal vestibule. The gas administering method is for use with a gas administering apparatus comprising a gas source that is operable to provide gas and a nasal vestibular portion arranged so as to receive the gas from the gas source. Further, the nasal vestibular portion is capable of releasing the gas into the nasal vestibule. The method comprises inserting the nasal vestibular portion into the nasal vestibule, forming a seal between the nasal vestibular portion and an inner surface of the nasal vestibule, administering an amount of a gas from the gas source at a constant flow rate into the nasal vestibule via the nasal vestibular portion, and administering an anesthetic to the patient. The anesthetic induces depression of a portion of the nervous system of the patient. Furthermore, the seal causes airway pressure buildup that is sufficient to prevent obstruction of the airway during depression of the portion of the nervous system and prevents escape of the gas from between the nasal vestibule and the nasal vestibular portion.

In one embodiment of the present invention, the gas administering method further comprises administering oxygen into the nasal vestibule via the nasal vestibular portion, prior to the administering of the anesthetic. More particularly, the oxygen is provided from a source of gas that is 100% oxygen. Alternatively, the oxygen is provided from a source of gas that is a mixture of oxygen and nitrogen.

In another embodiment of the present invention, the administering of an amount of a gas comprises administering 100% oxygen.

In another embodiment of the present invention, the administering of an amount of a gas comprises administering air.

In another embodiment of the present invention, the gas administering method further comprises detecting for an airway obstruction. More particularly, the detecting for an airway obstruction comprises placing a stethoscope over the trachea at the supra-sternal notch.

In another embodiment of the present invention, the gas administering method further comprises monitoring respiratory effort. More particularly, the monitoring respiratory effort is performed via an electrocardiogram monitor operating in a thoracic impedance mode.

In another embodiment of the present invention, the gas administering method further comprises retrieving anesthetic that is expired from the mouth of the patient. More particularly, the retrieving waist anesthetic comprises placing an anesthetic retrieving device over the face of the patient.

In general, the present invention further provides a gas administering method for administering a gas to an airway of a patient having a nasal vestibule. This method is for use with a gas administering apparatus comprising a gas source that is operable to provide gas at a constant flow rate and a nasal vestibular portion having a shape such that the nasal vestibular portion provides an outward force on an inner surface of the nasal vestibule, due to elasticity of the nasal vestibule, for retaining the nasal vestibular portion in the nasal vestibule. Further, the nasal vestibular portion is arranged so as to receive the gas from the gas source. Still further, the nasal vestibular portion is capable of releasing the gas. The method comprises inserting the nasal vestibular portion into the nasal vestibule thereby forming a seal between the nasal vestibular portion and an inner surface of the nasal vestibule, administering an amount of a gas at a constant flow rate into the nasal vestibule via the nasal vestibular portion, and administering an anesthetic to the patient. The anesthetic induces depression of a portion of the nervous system of the patient. Finally, the seal causes airway pressure buildup that is sufficient to prevent obstruction of the airway while under sedation and prevents escape of the gas between the nasal vestibule and the nasal vestibular portion.

In general, the present invention still further provides a gas administering method for administering gas to an airway of a patient having a nasal vestibule. This method is for use with an anesthetic administering apparatus comprising an anesthetic gas source that is operable to provide an anesthetic. The method comprises fastening a nasal vestibular portion to the anesthetic administering apparatus so as to receive the anesthetic gas from the anesthetic gas source (the nasal vestibular portion is capable of releasing the anesthetic gas into the nasal vestibule), inserting the nasal vestibular portion into the nasal vestibule, forming a seal between the nasal vestibular portion and an inner surface of the nasal vestibule, fastening a supplemental gas source to the anesthetic administering apparatus (the supplemental gas source is operable to provide a supplemental gas at a constant flow rate to the anesthetic administering apparatus) administering an amount of the supplemental gas from the supplemental gas source at a constant flow rate into the nasal vestibule, from the anesthetic administering apparatus, via the nasal vestibular portion, and administering an amount of the anesthetic gas from the anesthetic gas source into the nasal vestibule, from the anesthetic administering apparatus, via the nasal vestibular portion. The anesthetic gas comprises an amount of anesthetic sufficient to induce depression of at least a portion of the nervous system of the patient. Finally, the seal promotes airway pressure buildup that is sufficient to prevent obstruction of the airway during depression of the at least a portion of the nervous system and prevents escape of the anesthetic gas or the primary gas from between the nasal vestibule and the nasal vestibular portion.

In general, the present invention still further provides a gas administering system for administering gas to an airway of a patient having a nasal vestibule. The gas administering system comprises a gas source that is operable to provide gas at a constant flow rate and a nasal vestibular portion arranged so as to receive the gas from the gas source. The nasal vestibular portion is capable of releasing the gas into the nasal vestibule and is shaped to form a seal between the nasal vestibular portion and an inner surface of the nasal vestibule such that the gas released into the nasal vestibule causes airway pressure buildup sufficient to prevent obstruction of the airway during depression of at least a portion of the nervous system. Further, the seal prevents escape of the gas from between the nasal vestibule and the nasal vestibular portion.

In one embodiment of the present invention, the gas source comprises a primary gas source for providing a primary gas and a supplemental gas source that is operable to provide a supplemental gas. More particularly, the primary gas source may comprise an anesthetic gas providing device. Further, the primary gas source may comprise an oxygen providing device. Still further, the supplemental gas source may comprise an air providing device having a flow rate adjustment mechanism.

In another embodiment of the present invention, the gas administering system further comprises a respiration monitor.

In another embodiment of the present invention, the gas administering system further comprises a scavenging device for scavenging gas expired from the mouth of the patient.

In another embodiment of the present invention, the gas administering system further comprises a gas flow meter for measuring the gas flow rate of the gas provided by the gas source.

Additional advantages of the present invention will become apparent to those skilled in the art from the following detailed description of the preferred embodiments of the present invention. The invention itself, together with further objects and advantages, can be better understood by reference to the following detailed description and the accompanying drawings.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 1 illustrates a conventional system for treating sleep induced apnea by providing a continuous positive airway pressure through the nose;

FIG. 2 generally illustrates a preferred embodiment of a gas delivery apparatus according to the present invention;

FIG. 6 illustrates a gas delivery system in accordance with an exemplary embodiment of the present invention;

FIG. 9A is an exemplary subroutine for a step of increasing oxygen in the flow chart as illustrated in FIG. 8; FIG. 9B is another exemplary subroutine for a step of increasing oxygen in the flow chart as illustrated in FIG. 8;

FIG. 10A is an exemplary subroutine for a step of decreasing oxygen in the flow chart as illustrated in FIG. 8; FIG. 10B is another exemplary subroutine for a step of decreasing oxygen in the flow chart as illustrated in FIG. 8;

FIG. 11A is an exemplary subroutine for a step of administering anesthetic in the flow chart as illustrated in FIG. 8; FIG. 11B is another exemplary subroutine for a step of administering anesthetic in the flow chart as illustrated in FIG. 8;

FIG. 12A is an exemplary subroutine for a step of increasing the amount of administered anesthetic in the flow chart as illustrated in FIG. 8; FIG. 12B is another exemplary subroutine for a step of increasing the amount of administered anesthetic in the flow chart as illustrated in FIG. 8;

FIG. 13A is an exemplary subroutine for a step of decreasing the amount of administered anesthetic in the flow chart as illustrated in FIG. 8; FIG. 13B is another exemplary subroutine for a step of decreasing the amount of administered anesthetic in the flow chart as illustrated in FIG. 8.

Figure 3A:
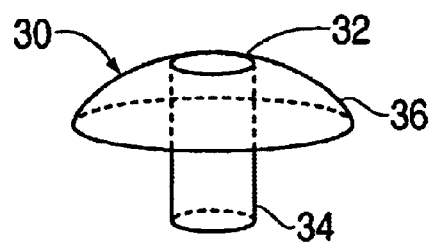
FIG. 3A illustrates an exemplary embodiment of a nasal vestibular portion that may be used with the gas delivery device in accordance with the present invention.

In the following description, for purposes of explanation, numerous specific details are set forth in order to provide a more thorough understanding of the present invention. It will be apparent, however, to one skilled in the art that the present invention may be practiced without the specific details.

DETAILED DESCRIPTION OF THE PREFERRED EMBODIMENTS

The following is a description of an exemplary method of and apparatus for enabling a patient to adequately respire at surgical levels of anesthesia without an invasive airway and manual or mechanized ventilation in accordance with the present invention.

During a pre-operative interview the patient is asked to confirm that he can breathe in and out through his nose.

The patient is then taken into the operating room and assisted in voluntarily positioning himself to comfort as appropriate through the anesthesia plan for facilitating the surgical intervention. Supine is the usual starting position for positions requiring intubation of the trachea. However, for superficial procedures in which the patient can be allowed to breath spontaneously, the patient can often be positioned awake and to comfort in the prone or lateral positions before induction of anesthesia. The airway, more often than not, is more easily maintained in these positions than in the supine position because of the lessened effects of gravity on the soft tissues (tongue and soft palate) that tend to collapse the airway. The awake patient will maintain a patent airway in any position, but the airway tends to collapse with deep sedation and general anesthesia. An invasive airway device can be traumatic and, in the case of an endotracheal tube, may cause more physiological disturbance than the surgery itself, if the anesthesia is not profound. On the other hand, a major cause of morbidity and mortality in anesthesia is related to the steps taken to control the patient's airway and to render it unreactive to the powerful stimulus of an endotracheal tube. For example, it has been reported more than once, that the patient has been paralyzed to facilitate intubation only to discover that the tube cannot be placed and the patient cannot be manually ventilated. The prudent anesthetist takes care not to impede the patient's own respiratory function without a well-considered reason and without thorough preparation. By using the method and apparatus in accordance with the present invention, the apparatus is inserted in the awake state, wherein a judgement can be usually made beforehand about the adequacy of the patient's respirations under deep sedation.

After the patient is appropriately positioned, conventional monitors may be attached to monitor the patient's vital signs, for example blood pressure, pulse rate, temperature, respiration rate, etc. A nasal insert device in accordance with the present invention is then snugly fitted into the nasal vestibule of the nose where the tissues are tougher and less sensitive than the mucosal lining of the turbinates and pharynx. Accordingly, an airtight seal is established fairly comfortably in the awake patient. This method of administering gas with the nasal insert device is less painful and traumatic to the patient than the conventional intubational method which uses an endotracheal tube. Further, a conventional nasal-pharyngeal airway is too long to be comfortably inserted into the deeper, more sensitive areas of the nose and nasopharynx.

The device of the present invention is then attached through standard connections to a closed anesthesia circuit, i.e., the pressure relief valve of the circuit is closed, and the flow rate of 100% oxygen is adjusted to the patient's comfort.

As the monitors are attached and preparation is made for induction of anesthesia, the awake patient is comfortably forced to breathe in through the nose and out through the mouth. The inhaled concentration of oxygen approaches 100% and nitrogen exhaled through the lungs is more effectively washed out, i.e. the period of denitrogenation, by the continuous flow of oxygen out through the mouth. Accordingly, the lungs are rapidly filled with oxygen and reserves of oxygen within the functional residual cavity of the lungs approaches a factor of ten increase, increasing dramatically the margin of safety as the critical induction period is approached. This is accomplished, by way of the present invention, in the comfortable, cooperative patient.

As preparation for induction of anesthesia approaches completion, the pulse oximeter usually approaches 100% oxygen saturation of the hemoglobin. The patient is then asked to take a breath through his nose. Nasal patency is confirmed by the deflation of a reservoir bag of the anesthesia circuit. At this point, the patient may be rapidly induced to deep sleep by a bolus of an induction drug, e.g. propofol. The airway pressure of the anesthesia circuit is seen to rise from zero to a positive value as determined by adjustment of the oxygen in-flow of the circuit. This pressure rise occurs as the soft tissues of the pharynx collapse into the airway and as the pressure generated through the nose stints up the soft palate against the base of the tongue to create a sealed pharyngeal passage pressurized somewhere between 5 and 20 cm of water pressure. This seal tends to release excess pressure before 20 cm of water pressure is achieved. As this is the threshold pressure in the pharynx beyond which gas is forced into the stomach, distension of the stomach with the attendant risk of reflux of gastric contents is naturally avoided.

The patient may become apneic at first, but soon spontaneous respirations resume. As the spontaneous respirations resume, the pressure gauge of a system in accordance with the present invention will rise and fall with inspiration and expiration.

At this point several options are available:

(A) If deep sedation-total intravenous anesthesia (TIVA) is to be maintained, then the patient may be allowed to breathe spontaneously with a system in accordance with the present invention that is pressured sufficiently by a constant gas flow rate so as to prevent airway obstruction. Detection of partial airway obstruction is best detected by fixed-placement of a stethoscope over the trachea at the supra-sternal notch. In addition, respiratory effort can be monitored by thoracic impedance mode of the electrocardiogram monitor.

(B) If general inhalation anesthesia is planned, then a scavenging system may be established by placing the standard anesthesia face mask over the nasal insert and its connections and then connecting the mask by standard corrugating tubing to the scavenger port of the anesthesia machine.

(C) If intubation is required, the nasal insert and its connection to the anesthesia circuit can be left in place while the scavenging mask is removed. This constant gas flow through the nose floods the pharynx with oxygen and the gas anesthetic to maintain oxygenation and anesthetic depth during even a prolonged intubation procedure. If at this point, the patient were to be paralyzed with a muscle relaxant and rendered totally apneic, oxygenation would still be potentially satisfactory for periods of time in excess of 20 minutes (without manual ventilation) by the process of "mass movement" of 100% oxygen from the pharynx into the vacuum in the lungs created by absorption of oxygen from the lungs into the blood. Thus, the method in accordance with the present invention routinely adds a large method of safety even for the unexpected difficult airway, which can be so disastrous to the patient.

FIG. 2 generally illustrates an exemplary embodiment of a gas delivery apparatus according to the present invention. As illustrated in FIG. 2, the gas delivery apparatus 202 includes two branches of tubing 206 that provide gas to a gas delivery device 208. Gas delivery device 208 includes two nasal vestibular portions 210 and 212 that are inserted into the nasal vestibules 214 of the patient 204. A scavenging device 216 may be used in conjunction with the gas delivery apparatus, and will be described in greater detail below. The gas delivery apparatus 202 further includes a gas input port 218 that receives gas from a gas source.

Gas delivery device 208 differs from airflow delivery device 108 of FIG. 1 in that gas delivery device 208 does not have ventilation holes.

Figure 3B:
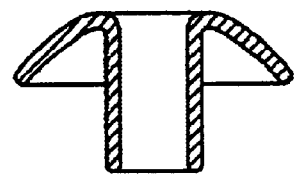
FIG. 3B is a cross-sectional view of the nasal vestibular portion as depicted in FIG. 3A.
Figure 4A:
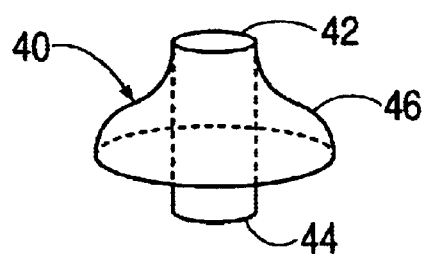
FIG. 4A illustrates another exemplary embodiment of a nasal vestibular portion that may be used with the gas delivery device in accordance with the present invention.
Figure 4B:
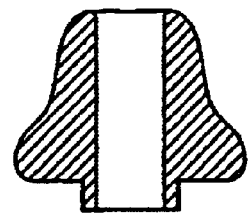
FIG. 4B is a cross-sectional view of the nasal vestibular portion as depicted in FIG. 4A.

Vestibular portions 210 and 212 can be any shape that may: be inserted into the nasal vestibule of the patient; provide a seal between the gas delivery device 208 and an inner surface of the nasal vestibule; and administer an amount of a gas into the nasal vestibule via the nasal vestibular portion, wherein the seal promotes airway pressure buildup that is sufficient to prevent obstruction of the airway during depression of the portion of the nervous system and prevents escape of the gas from between the nasal vestibule and the gas delivery device 208. FIGS. 3A and 4A illustrate exemplary embodiments of nasal vestibular portions that may be used with the gas delivery device in accordance with the present invention. FIGS. 3B and 4B are cross-sectional illustrations of FIGS. 3A and 4A, respectively.

As illustrated in FIG. 3A, the nasal vestibular portion 30 includes a gas flow tube portion 34, a gas delivery port 32 and a rounded protruding portion 36 that is shaped so as to fit into a nasal vestibule and form a seal with the inner surface of the nasal vestibule. In particular, the rounded protruding portion 36 prevents gas from escaping from the nasal vestibule to outside of the nasal vestibule.

FIG. 4A is a second exemplary embodiment of a nasal vestibular portion. A nasal vestibular portion 40 includes a gas flow portion 44, a gas delivery port 42 and a bell-shaped protruding portion 46. Similar to the portion 36 of FIG. 3A, bell-shaped protruding portion 46 is shaped so as to form a seal with the inner surface of the nasal vestibule thereby preventing gas from escaping and the nasal vestibule.

Figure 5A:
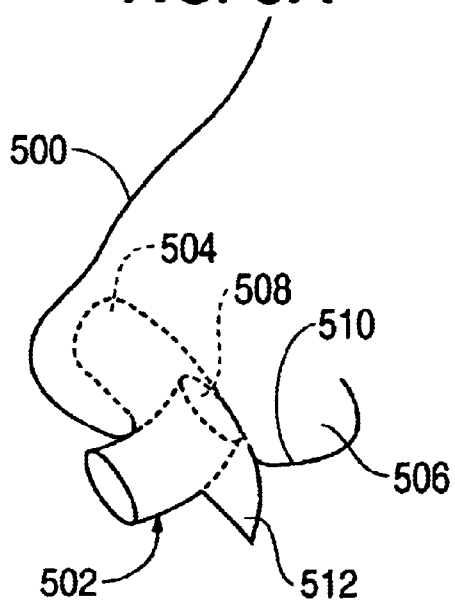
FIGS. 5A and 5B illustrate how an embodiment of a nasal vestibular portion according to the present invention is inserted into the nasal vestibule of the patient.
Figure 5B:
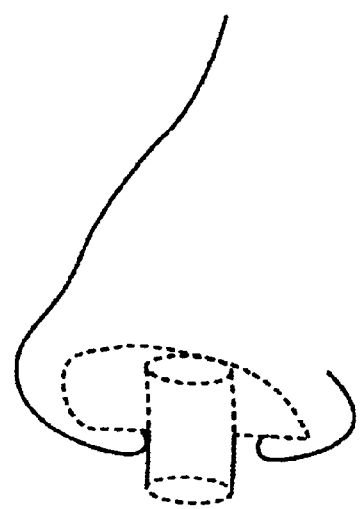

FIGS. 5A and 5B illustrate insertion of a nasal vestibular portion into the nasal vestibule. In the figures, a nasal vestibular portion 502 is inserted into the nose 500. In particular, a superior pole 504 is inserted into the nasal vestibule 506. A nasal vestibular airway 508 is then rotated over the inferior nostril rim 510, and the sharp angle of the wedge 512 locks the nasal vestibular airway 508 in place in the nasal vestibule 506. Sealing forces of the nasal vestibular airway are against the inner surfaces of the nose to provide an outward force on the inner surfaces of the nose.

FIG. 6 illustrates a gas delivery system in accordance with an exemplary embodiment of the present invention. As depicted in FIG. 6, the gas delivery system 600 includes a gas circuit 602 in addition to a nasal vestibular portion 604 for administering gas into the nasal vestibule of the patient, a positive pressure gauge 606 and a supplemental gas providing system 608.

Figure 7:
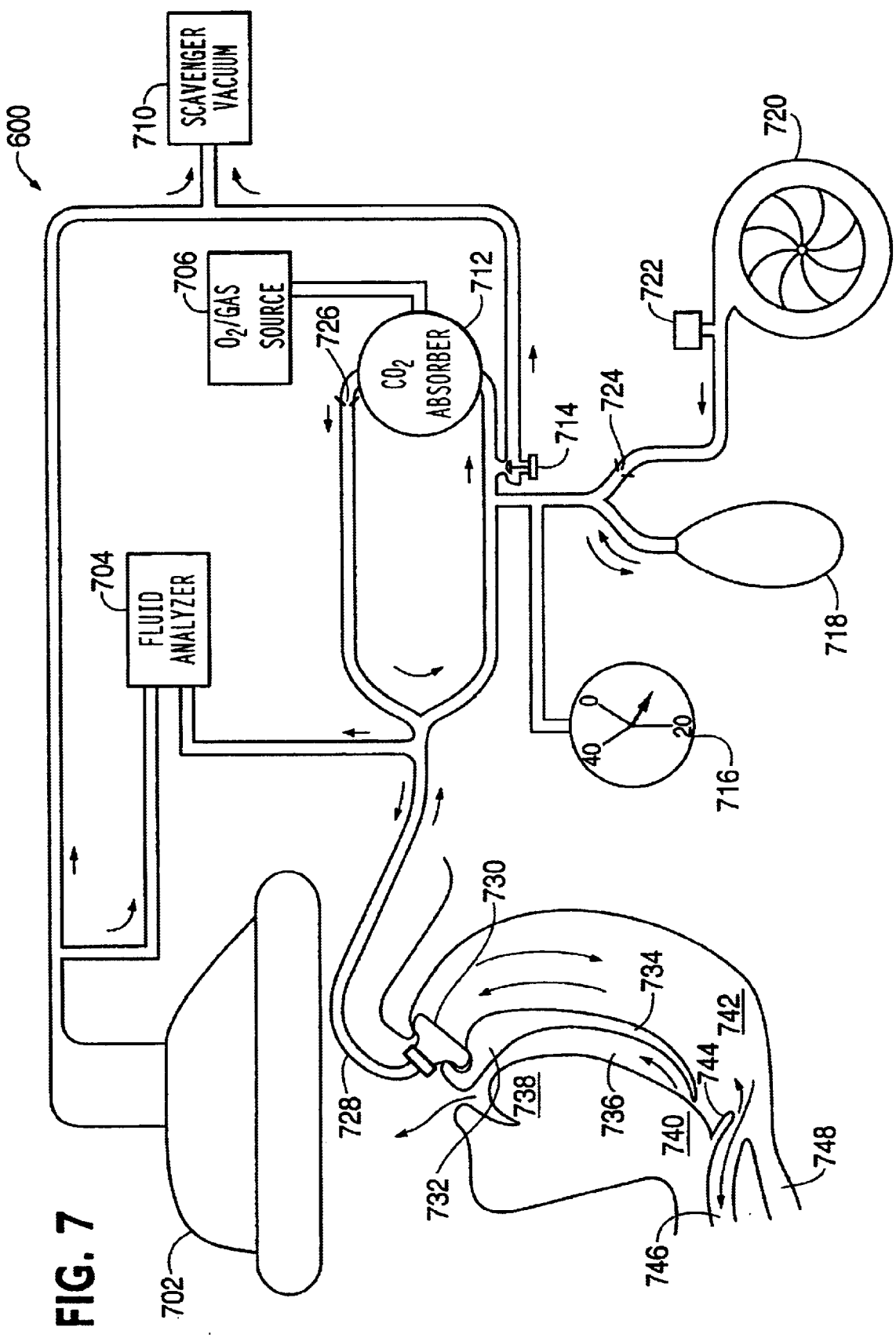
FIG. 7 is a more detailed illustration of a gas delivery system in accordance with the present invention.

FIG. 7 is a more detailed illustration of a gas delivery system in accordance with the present invention. As depicted in FIG. 7, gas delivery system 600 includes a scavenging device 702, a gas analyzer 704, a primary gas source 706, a scavenging vacuum 710, a $CO_2$ absorber 712, a valve 714, a positive pressure gauge 716, a respiration monitoring device 718, a supplemental gas source 720, a valve 722, a valve 724, a valve 726, gas delivery hose 728, and a nasal vestibular portion 730. Tubing 750 connects, in gas flow communication, scavenging device 702, gas analyzer 704, primary gas source 706, scavenging vacuum 710, $CO_2$ absorber 712, valve 714, and valve 726. Tubing 752 connects, in gas flow communication, positive pressure gauge 716, respiration monitoring device 718, supplemental gas source 720, valve 722, and valve 724.

Item 754 is a connection point for tubing 752 to connect, in gas flow communication, with tubing 750. Similarly, item 756 is a connection point for tubing 728 to connect, in gas flow communication, with tubing 750. Accordingly, the tubing 752, and its associated devices, and tubing 728 and its associated nasal vestibular portion may be attached to a pre-existing gas delivery system comprising a scavenging device, a gas analyzer, a primary gas source, scavenging vacuum, and $CO_2$ absorber. Alternatively, items 756 and 754 need not exist, wherein the entire gas delivery system 600 is unitary.

A scavenging portion of gas delivery system 600 includes scavenging device 702 and scavenger vacuum 710. An exemplary embodiment of scavenging device 702 is a scavenging mask, which may be placed over the face of the patient. The scavenger vacuum 710 provides suction to retrieve gas expired through the mouth of the patient and thereby prevent leakage of an anesthetic gas, for example, into the surgical field. Furthermore, a portion of the scavenged gasses are analyzed by gas analyzer 704 in order to determine the composition of the gasses. Although a scavenging portion is not required for the gas delivery system in accordance with the present invention, its addition may be desired to prevent contamination of expired anesthetic into the surgical field and to reduce fire hazards resulting therefrom.

Gas source 706 provides the primary gas to be administered to the patient. The primary gas is oxygen used to oxygenate a patient. Further, the primary gas may include an anesthetic medication to be administered to the patient. Still further, the primary gas may include air, nitrogen, or another gas to be administered to the patient. Alternatively, the primary gas may be a mixture of oxygen, anesthetic medication, and another gas.

Valve 726 comprises a one-way valve which forces gas to flow unidirectional, thereby creating a circular flow of gas through $CO_2$ absorber 712. $CO_2$ absorber 712, reduces the amount of $CO_2$ within the gas circulated through the gas delivery system 600.

Supplemental gas source 720 may be an air generator for providing a constant flow rate of air. Valve 722 comprises an adjustable valve, for example, a manually adjustable valve, for adjusting the gas flow rate provided by supplemental gas source 720. Valve 724 is a unidirectional valve that prevents back flow of gas into supplemental gas source 720.

Reservoir 718 is expandable and contractible in response to the divergence of gas flowing therein, respectively. Reservoir 718 may therefore be used as a visual indicator of the patient's respiration.

Positive pressure gauge 716, monitors the positive pressure of the gas within gas delivery system 600. Positive pressure gauge 716 should be capable of measuring pressure between 0 and 20 cm of water. Specifically, because pressures in excess of 20 cm of water has been shown to blow air into the stomach, positive pressure gauge 716 must be able to measure at least 20 cm of water. More importantly, positive pressure gauge 716 in should display the detected pressure at a precision that would readily communicate the difference between an inspiration and an expiration of the patient.

An exemplary method of operation of gas delivery system 600 as illustrated in FIG. 7 will now be explained with reference to the flow charts of FIG. 8 through FIG. 13B.

Figure 8:
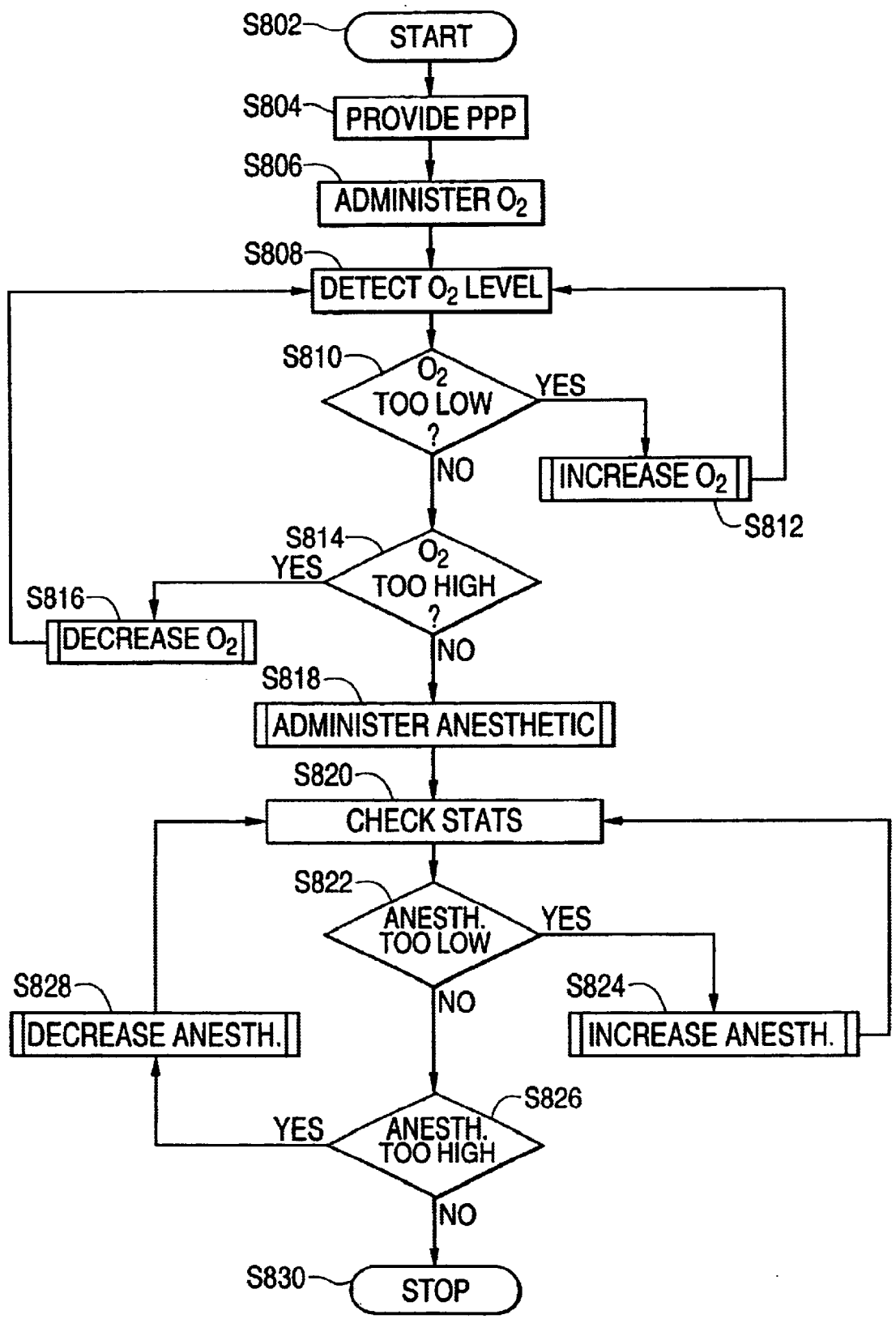
FIG. 8 is a flow chart detailing an exemplary method of operation of gas delivery system as illustrated in FIG. 7.

Referring to FIG. 8, after nasal vestibular portion 730 has been inserted into the nasal vestibule of the patient, the process is started (S802), and an alternating positive airway pressure is provided to the patient (S804). In particular, supplemental gas source 720 provides a supplemental gas, the flow rate of which is constant and is manually set by manual adjustment valve 722. In this exemplary embodiment, the supplemental gas is air. The gas enters the gas circuit 602 via unidirectional valve 724 and eventually enters the nasopharynx 742 of the patient by way of nasal vestibular portion 730. The gas flow rate is set to achieve a positive pressure that is less than 20 cm of water, which is monitored through the positive pressure gauge 716. The gas flows from nasopharynx 742, past the epiglottis 744, into the trachea 746 and continues into the lungs. Expiration of the patient provides back flow of expired gas back through nasopharynx 742 and through the oral cavity 736. Gas in oral cavity 746 is expired out through the mouth, whereas back flow of gas in nasopharynx 742 returns into nasal vestibular portion 730 and returns into the gas delivery system 600. Respirations and expirations of the patient are monitored via constriction and expansion of reservoir 818. Further, as discussed above, a scavenging system may be used wherein, for example, scavenging mask 702 is placed over the patient's face. Scavenging mask 802, as operably connected to the scavenging vacuum 710, scavenges any gasses that may be respired from the patient. Furthermore, gas analyzer 704 analyses a portion of the scavenged gasses in order to determine the composition thereof.

Returning to FIG. 8, once the PPP is established, oxygen is administered (S806). In this exemplary embodiment, referring to FIG. 7, a second gas source, which is primary gas source 806 provides oxygen, which is ultimately administered to the patient via nasal vestibular portion 730. However, primary gas source 806 may additionally be constructed so as to provide oxygen via a mixture of oxygen and other gasses such as nitrogen or air. Furthermore, primary gas source 806 might not be needed if supplemental gas source 720 is operable to provide sufficient oxygen to the patient.

Once the oxygen has been administered to the patient, the patient's oxygen levels are monitored (S808) by any conventional method, such as with a pulse oximeter. If the oxygen level is determined to be too low (S818), then the oxygen provided to the patient is increased (S812). On the contrary, if the oxygen level of the patient is determined to be too high (S814), then the oxygen level is decreased (S816). Accordingly, a flow rate of gas from primary gas source 806 may be adjusted until the patient is receiving an appropriate amount of oxygen.

If the oxygen supply must be increased, the constant flow rate of the supplemental gas from the supplement gas source 720 should be adjusted accordingly in order to maintain a constant total gas flow rate, which is the sum of the supplemental gas flow rate and the oxygen flow rate. Ideally, if the oxygen flow rate is to be increased by a predetermined amount, then the gas flow rate of the supplemental gas source 720 should be concurrently decreased by an equal amount in order to maintain a constant total gas flow rate of the combined oxygen and supplemental gas. A system may be easily constructed with conventional technology so as to easily accomplished this aspect. In particular, such a system may include a servo system for automatically adjusting the flow rates of the supplemental gas source 720 and the primary gas source 806 so as to maintain a constant total gas flow rate.

Nevertheless, when it is determined that the oxygen level supplied to the patient is too low (S810) wherein the oxygen supply must be increased (S812), the two exemplary procedures as illustrated in FIGS. 9A and 9B may be followed. In particular, FIGS. 9A and 9B illustrate exemplary procedures, wherein the increase in oxygen and the decrease in the supplemental gas are not performed simultaneously. These procedures therefore are not ideal because the total gas flow rate changes slightly when one gas flow rate is decreased but before the other gas flow rate is increased. However, the systems required to perform the procedures described with respect to FIGS. 9A and 9B may be less complicated and less expensive to construct because a servo system for automatically adjusting the flow rates would not be required.

As illustrated in FIG. 9A, at the start of the procedure (S902), the gas flow rate is determined (S904). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the oxygen flow rate is then increased by a predetermined amount (S906). Subsequently, in order to maintain a constant gas flow rate, the supplemental gas is decreased in an equal amount (S908), and process stops (S910).

An alternate procedure is illustrated in FIG. 9B. At the start of the procedure (S902), the gas flow rate is determined (S904). Then, the supplemental gas is decreased by a predetermined amount (S912). Subsequently, in order to maintain a constant gas flow rate, the oxygen flow rate is increased in an equal amount (S914), and process stops (S916).

Returning to FIG. 8, wherein it is determined that the oxygen administered to the patient needs to be decreased (S816), ideally, if the oxygen flow rate is decreased by a predetermined amount, then the gas flow rate of the supplemental gas source 720 should be concurrently increased by an equal amount in order to maintain a constant total gas flow rate of the combined oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when it is determined that the oxygen level supplied to the patient is too high (S814) wherein the oxygen supply must be increased (S816), the two exemplary procedures as illustrated in FIGS. 10A and 10B may be followed. In particular, FIGS. 10A and 10B illustrate exemplary procedures, wherein the decrease in oxygen and the increase in the supplemental gas are not performed simultaneously. These procedures therefore are not ideal because the total gas flow rate changes slightly when one gas flow rate is decreased but before the other gas flow rate is increased. However, the systems required to perform the procedures described with respect to FIGS. 10A and 10B may be less complicated and less expensive to construct because a servo system for automatically adjusting the flow rates would not be required.

As illustrated in FIG. 10A, at the start of the procedure (S1002), the gas flow rate is determined (S1004). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the oxygen flow rate is then decreased by a predetermined amount (S1006). Subsequently, in order to maintain a constant gas flow rate, the supplemental gas is increased in an equal amount (S1008), and process stops (S1010).

An alternate procedure is illustrated in FIG. 10B. At the start of the procedure (S1002), the gas flow rate is determined (S1004). Then, the supplemental gas is increased by a predetermined amount (S1012). Subsequently, in order to maintain a constant gas flow rate, the oxygen flow rate is decreased in an equal amount (S1014), and process stops (S1016).

Returning to FIG. 8, once the oxygen level of the patient is appropriate, a general anesthetic may be administered (S818). In this exemplary embodiment, the anesthetic is administered through inhalation.

Ideally, if the anesthetic is administered at a predetermined flow rate, then the gas flow rate of the gas from supplemental gas source 720 in addition to the oxygen flow rate from the primary gas source 706 should be decreased by an equal amount in order to maintain a constant gas flow rate of the combined anesthetic, oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when the anesthetic is to be administered to the patient (S818), the two exemplary procedures as illustrated in FIGS. 11A and 11B may be followed. In particular, FIGS. 11A and 11B illustrate exemplary procedures, wherein the anesthetic is administered in a predetermined amount non-concurrently with a decreasing of the oxygen flow rate and the supplemental gas flow rate by the predetermined amount. These procedures therefore are not ideal because the total gas flow rate changes slightly when one gas flow rate is decreased but before the other gas flow rate is increased. However, the systems required to perform the procedures described with respect to FIGS. 11A and 11B may be less complicated and less expensive to construct because a servo system for automatically adjusting the flow rates would not be required.

As illustrated in FIG. 11A, at the start of the procedure (S1102), the gas flow rate is determined (S1104). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the flow rate of the oxygen and the supplemental gas is then decreased by a predetermined amount (S1106). Specifically, the flow rate of the oxygen may be decreased by the predetermined amount, the flow rate of the supplemental gas may be decreased by the predetermined amount, or some portion of each of the oxygen flow rate and supplemental gas flow rate may be decreased such that the total flow rate decrease is equal to the predetermined amount. Subsequently, in order to maintain a constant gas flow rate, the anesthetic is administered in an equal amount (S1108), and process stops (S1110).

An alternate procedure is illustrated in FIG. 1B. At the start of the procedure (S1102), the gas flow rate is determined (S1104). Then, the anesthetic is administered by a predetermined amount (S1112). Subsequently, in order to maintain a constant gas flow rate, the flow rate of the oxygen and the supplemental gas is decreased by a predetermined amount (S1114), and process stops (S1116).

Returning to FIG. 8, once the anesthetic has been administered (S818), the patient is monitored so as to determine whether a sufficient amount of anesthetic is being administered (S820). If it is determined that the amount of anesthetic provided to the patient is too low (S822) then the amount of anesthetic provided to the patient is increased (S824). Alternatively, if it is determined that the amount of anesthetic provided to the patient is too high (S826), then the amount of anesthetic provided to the patient is decreased (S828).

Ideally, if the anesthetic is to be increased by a predetermined flow rate, then the gas flow rate of the gas from supplemental gas source 720 in addition to the oxygen flow rate from the primary gas source 706 should be decreased by an equal amount in order to maintain a constant gas flow rate of the combined anesthetic, oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when the anesthetic is to be increased (S824), the two exemplary procedures as illustrated in FIGS. 12A and 12B may be followed. In particular, FIGS. 12A and 12B illustrate exemplary procedures, wherein the anesthetic is increased in a predetermined amount non-concurrently with a decreasing of the oxygen flow rate and the supplemental gas flow rate by the predetermined amount. These procedures therefore are not ideal because the total gas flow rate changes slightly when one gas flow rate is decreased but before the other gas flow rate is increased. However, the systems required to perform the procedures described with respect to FIGS. 12A and 12B may be less complicated and less expensive to construct because a servo system for automatically adjusting the flow rates would not be required.

As illustrated in FIG. 12A, at the start of the procedure (S1202), the gas flow rate is determined (S1204). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the flow rate of the anesthetic is then increased by a predetermined amount (S1206). Subsequently, in order to maintain a constant gas flow rate, the flow rate of the oxygen and the supplemental gas is decreased by the predetermined amount (S1208). Specifically, the flow rate of the oxygen may be decreased by the predetermined amount, the flow rate of the supplemental gas may be decreased by the predetermined amount, or some portion of each of the oxygen flow rate and supplemental gas flow rate may be decreased such that the total flow rate decrease is equal to the predetermined amount. The process then stops (S1210).

An alternate procedure is illustrated in FIG. 12B. At the start of the procedure (S1202), the gas flow rate is determined (S1204). Then, the flow rate of the oxygen and the supplemental gas is decreased by a predetermined amount (S1212). Subsequently, in order to maintain a constant gas flow rate, the anesthetic is increased by the predetermined amount (S1214), and process stops (S1216).

Returning to FIG. 8, wherein it is determined that the anesthetic administered to the patient needs to be decreased (S828), ideally, if the anesthetic is to be decreased by a predetermined flow rate, then the gas flow rate of the gas from supplemental gas source 720 in addition to the oxygen flow rate from the primary gas source 706 should be increased by an equal amount in order to maintain a constant gas flow rate of the combined anesthetic, oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when the anesthetic is to be decreased (S828), the two exemplary procedures as illustrated in FIGS. 13A and 13B may be followed. In particular, FIGS. 13A and 13B illustrate exemplary procedures, wherein the anesthetic is decreased in a predetermined amount non-concurrently with an increasing of the oxygen flow rate and the supplemental gas flow rate by the predetermined amount. These procedures therefore are not ideal because the total gas flow rate changes slightly when one gas flow rate is decreased but before the other gas flow rate is increased. However, the systems required to perform the procedures described with respect to FIGS. 13A and 13B may be less complicated and less expensive to construct because a servo system for automatically adjusting the flow rates would not be required.

As illustrated in FIG. 13A, at the start of the procedure (S1302), the gas flow rate is determined (S1304). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the flow rate of the oxygen and the supplemental gas is then increased by a predetermined amount (S1306). Specifically, the flow rate of the oxygen may be increased by the predetermined amount, the flow rate of the supplemental gas may be increased by the predetermined amount, or some portion of each of the oxygen flow rate and supplemental gas flow rate may be increased such that the total flow rate increase is equal to the predetermined amount. Subsequently, in order to maintain a constant gas flow rate, the flow rate of the anesthetic is decreased by the predetermined amount (S1308). The process then stops (S1310).

An alternate procedure is illustrated in FIG. 13B. At the start of the procedure (S1202), the gas flow rate is determined (S1304). Then, the anesthetic is decreased by a predetermined amount (S1312). Subsequently, in order to maintain a constant gas flow rate, the flow rate of the oxygen and the supplemental gas is increased by the predetermined amount (S1314), and process stops (S1316).

Steps S818 through S830 are repeated until the proper amount of anesthetic is provided to the patient, wherein the process stops (S830).

If the anesthetic is to be administered intravenously, then a simplified embodiment of the present invention may be used. In particular, the oxygen provided to the patient is adjusted to a proper level while the supplemental gas provider administers supplemental gas to maintain a constant gas flow rate. In other words, the oxygen and supplemental gas may not be further adjusted so as to accommodate an additional gas flow of anesthetic, because the anesthetic has been administered intravenously.

In the exemplary embodiment described above, supplemental gas source 706 provides both oxygen and anesthetic. In an alternative embodiment, two separate gas sources may be provided, one for administering oxygen and one for administering anesthetic. In another embodiment, supplemental gas source only administers oxygen, wherein an inhalation anesthetic is not required.

Further, the device according to the present invention can be tolerated without anesthesia or sedation. It is less likely to cause claustrophobia. Further, while existing devices are cumbersome and surround the face and head with a mask and straps, and a bag, the nasal vestibular airway can be paired and worn like eyeglasses with hooks or straps over the ears.

Furthermore, the nasal vestibular airway according to the present invention may be applied to deeply sedated patients in dental surgery. The device of the present application may even be considered for use in veterinary medicine, where there is no satisfactory means of assisting a spontaneously breathing but respiratory-compromised animal.

The above embodiments of the present invention have been described with respect to specific features thereof. However, it is noted that the scope of the present invention is defined in the following claims, and should not be limited by the specific embodiments described above.

What is claimed is:

1. A gas administering method for administering gas to an airway of a patient having a face, amount, a nervous system and a nasal vestibule and for use with a gas administering apparatus comprising a gas source that is operable to provide gas and a nasal vestibular portion arranged so as to receive the gas from the gas source, the nasal vestibular portion being capable of releasing the gas into the nasal vestibule, said method comprising:

inserting the nasal vestibular portion into the nasal vestibule;

forming a seal between the nasal vestibular portion and a surface of the nasal vestibule;

administering an amount of a gas from the gas source at a constant flow rate into the nasal vestibule via the nasal vestibular portion such that the seal causes airway pressure buildup that is sufficient to prevent obstruction of the airway during depression of at least a portion of the nervous system and prevents escape of the gas from between the nasal vestibule and the nasal vestibular portion; and administering an anesthetic to the patient to induce depression of the at least a portion of the nervous system of the patient.

2. The gas administering method of claim 1, further comprising administering oxygen into the nasal vestibule via the nasal vestibular portion, prior to said administering of the anesthetic.

3. The gas administering method of claim 2, wherein said administering oxygen comprises administering 100% oxygen.

4. The gas administering method of claim 2, wherein said administering oxygen comprises administering a mixture of oxygen and nitrogen.

5. The gas administering method of claim 1, wherein said administering of an amount of a gas comprises administering 100% oxygen.

6. The gas administering method of claim 1, wherein said administering of an amount of a gas comprises administering air.

7. The gas administering method of claim 1, further comprising detecting for an airway obstruction.

8. A gas administering method of claim 7, wherein said detecting for an airway obstruction comprises placing a stethoscope over the trachea at the supra-sternal notch.

9. The gas administering method of claim 1, further comprising monitoring respiratory effort.

10. The gas administering method of claim 9, wherein said monitoring respiratory effort is performed via electrocardiogram monitor operating in a thoracic impedance mode.

11. The gas administering method of claim 1, further comprising retrieving anesthetic that is expired from the mouth of the patient.

12. The gas administering method of claim 11, wherein said retrieving anesthetic comprises placing an anesthetic retrieving device over the face of the patient.

13. A gas administering method for administering a gas to an airway of a patient having a nasal vestibule and for use with a gas administering apparatus comprising a gas source that is operable to provide gas at a constant flow rate and a nasal vestibular portion having a shape such that the nasal vestibular portion provides a force on a surface of the nasal vestibule, due to elasticity of the nasal vestibule, for retaining the nasal vestibular portion in the nasal vestibule, the nasal vestibular portion being arranged so as to receive the gas from the gas source, the nasal vestibular portion being capable of releasing the gas, said method comprising:

inserting the nasal vestibular portion into the nasal vestibule thereby forming a seal between the nasal vestibular portion and a surface of the nasal vestibule;

administering an amount of a gas at a constant flow rate into the nasal vestibule via the nasal vestibular portion such that the seal causes airway pressure buildup that is sufficient to prevent obstruction of the airway while under sedation and prevents escape of the gas between the nasal vestibule and the nasal vestibular portion, and administering an anesthetic to the patient to induce depression of at least a portion of the nervous system of the patient.

14. A gas administering method of administering gas to an airway of a patient having a nasal vestibule and for use with an anesthetic administering apparatus comprising an anesthetic gas source that is operable to provide an anesthetic, said method comprising:

fastening a nasal vestibular portion to the anesthetic administering apparatus so as to receive the anesthetic gas from the anesthetic gas source, the nasal vestibular portion being capable of releasing the anesthetic gas into the nasal vestibule, inserting the nasal vestibular portion into the nasal vestibule;

forming a seal between the nasal vestibular portion and a surface of the nasal vestibule;

fastening a supplemental gas source to the anesthetic administering apparatus, the supplemental gas source being operable to provide a supplemental gas at a constant flow rate to the anesthetic administering apparatus;

administering an amount of the supplemental gas from the supplemental gas source at a constant flow rate into the nasal vestibule, from the anesthetic administering apparatus, via the nasal vestibular portion, such that the seal promoters airway pressure buildup that is sufficient to prevent obstruction of the airway during depression of at least a portion of the nervous system and prevents escape of the anesthetic gas or the supplemental gas from between the nasal vestibule and the nasal vestibular portion; and administering, from the anesthetic gas source via the nasal vestibular portion, an amount of the anesthetic gas sufficient to induce depression of the at least a portion of the nervous system of the patient.

15. A gas administering system for administering gas to an airway of a patient having a mouth and a nasal vestibule, said gas administering system comprising:

a gas source that is operable to provide gas at a constant flow rate; and a nasal vestibular portion arranged so as to receive the gas from said gas source, said nasal vestibular portion being capable of releasing the gas into the nasal vestibule, said nasal vestibular portion being shaped to from a seal between the nasal vestibule causes airway pressure buildup sufficient to prevent obstruction of the airway during depression of at least a portion of the nervous system, wherein the seal prevents escape of the gas from between the nasal vestibule and said nasal vestibular portion.

16. The gas administering system of claim 15, wherein said gas source comprises a primary gas source for providing a primary gas; and a supplemental gas source that is operable to provide a supplemental gas.

17. The gas administering system of claim 16, wherein said primary gas source comprises an anesthetic gas providing device.

18. The gas administering system of claim 16, wherein said primary gas source comprises an oxygen providing device.

19. The gas administering system of claim 16, wherein said supplemental gas source comprises an air providing device comprising a flow rate adjustment mechanism.

20. The gas administering system of claim 15, further comprising a respiration monitor.

21. The gas administering system of claim 15, further comprising a scavenging device for scavenging gas expired from the mouth of the patient.

22. The gas administering system of claim 15, further comprising a gas flow meter for measuring the gas flow rate of the gas provided by said gas source.

23. A gas administering method for administering gas to an airway of a patient having a face, a mouth, a nervous system and a nasal vestibule and for use with a gas administering apparatus comprising a gas source that is operable to provide gas and a nasal vestibular portion arranged so as to receive the gas from the gas source, the nasal vestibular portion being capable of releasing the gas into the nasal vestibule, said method comprising:

inserting the nasal vestibular portion into the nasal vestibule;

forming a seal between the nasal vestibular portion and a surface of the nasal vestibule;

administering an amount of a gas from the gas source at a flow rate into the nasal vestibule via the nasal vestibular portion such that the seal causes airway pressure buildup that is sufficient to prevent obstruction of the airway during depression of at least a portion of the nervous system and prevents escape of the gas from between the nasal vestibule and the nasal vestibular portion; and administering an anesthetic to the patient to induce depression of the at least a portion of the nervous system of the patient.

24. The gas administering method of claim 23, further comprising administering oxygen into the nasal vestibule via the nasal vestibular portion, prior to said administering of the anesthetic.

25. The gas administering method of claim 24, wherein said administering oxygen comprises administering 100% oxygen.

26. The gas administering method of claim 24, wherein said administering oxygen comprises administering a mixture of oxygen and nitrogen.

27. The gas administering method of claim 23, wherein said administering of an amount of a gas comprises administering 100% oxygen.

28. The gas administering method of claim 23, wherein said administering of an amount of a gas comprises administering air.

29. The gas administering method of claim 23, further comprising detecting for an airway obstruction.

30. The gas administering method of claim 29, wherein said detecting for an airway obstruction comprises placing a stethoscope over the trachea at the supra-sternal notch.

31. The gas administering method of claim 23, further comprising monitoring respiratory effort.

32. The gas administering method of claim 31, wherein said monitoring respiratory effort is performed via electrocardiogram monitor operating in a thoracic impedance mode.

33. The gas administering method of claim 23, further comprising retrieving anesthetic that is expired from the mouth of the patient.

34. The gas administering method of claim 33, wherein said retrieving anesthetic comprises placing an anesthetic retrieving device over the face of the patient.

35. A gas administering method for administering a gas to an airway of a patient having a nasal vestibular and for use with a gas administering apparatus comprising a gas source that is operable to provide gas at a flow rate and a nasal vestibular portion having a shape such that the nasal vestibular portion provides a force on a surface of the nasal vestibule, due to elasticity of the nasal vestibule, for retaining the nasal vestibular portion in the nasal vestibule, the nasal vestibular portion being arranged sa as to receive the gas from the gas source, the nasal vestibular portion being capable of releasing the gas, said method comprising:

inserting the nasal vestibular portion into the nasal vestibule thereby forming a seal between the nasal vestibular portion and a surface of the nasal vestibule;

administering an amount of a gas at a flow rate into the nasal vestibule via the nasal vestibular portion such that the seal causes airway pressure buildup that is sufficient to prevent obstruction of the airway while under sedation and prevents escape of the gas between the nasal vestibule and the nasal vestibular portion; and administering an anesthetic to the patient to induce depression of at least a portion of the nervous system of the patient.

36. A gas administering method for administering gas to an airway of a patient having a nasal vestibule and for use with an anesthetic administering apparatus comprising an anesthetic gas source that is operable to provide an anesthetic, said method comprising:

fastening a nasal vestibular portion to the anesthetic administering apparatus so as to receive the anesthetic gas from the anesthetic gas source, the nasal vestibular portion being capable of releasing the anesthetic gas into the nasal vestibule;

inserting the nasal vestibular portion into the nasal vestibule;

forming a seal between the nasal vestibular portion and a surface of the nasal vestibule;

fastening a supplemental gas source to the anesthetic administering apparatus, the supplemental gas source being operable to provide a supplemental gas at a flow rate to the anesthetic administering apparatus;

administering an amount of the supplemental gas from the supplemental gas source at a flow rate into the nasal vestibule, from the anesthetic administering apparatus, via the nasal vestibular portion, such that the seal promotes airway pressure buildup that is sufficient to prevent obstruction of the airway during depression of at least a portion of the nervous system and prevents escape of the anesthetic gas or the supplemental gas from between the nasal vestibule and the nasal vestibular portion; and administering, from the anesthetic gas source via the nasal vestibular portion, an amount of the anesthetic gas sufficient to induce depression of the at least a portion of the nervous system of the patient.

37. A gas administering system for administering gas to an airway of a patient having a method and a nasal vestibule, said gas administering system comprising:

a gas source that is operable to provide gas at a flow rate; and a nasal vestibular portion arranged so as to receive the gas from said gas source, said nasal vestibular portion being capable of releasing the gas into the nasal vestibule, said nasal vestibular portion being shaped to form a seal between the nasal vestibular portion and a surface of the nasal vestibule such that the gas released into the nasal vestibule causes airway pressure buildup sufficient to prevent obstruction of the airway during depression of at least a portion of the nervous system, wherein the seal prevents escape of the gas from between the nasal vestibule and said nasal vestibular portion.

38. The gas administering system of claim 37, wherein said gas source comprises a primary gas source for providing a primary gas, and a supplemental gas source that is operable to provide a supplemental gas.

39. The gas administering system of claim 38, wherein said primary gas source comprises an anesthetic gas providing device.

40. The gas administering system of claim 38, wherein said primary gas source comprises an oxygen providing device.

41. The gas administering system of claim 38, wherein said supplemental gas source comprises an air providing device comprising a flow rate adjustment mechanism.

42. The gas administering system of claim 37, further comprising a respiration monitor.

43. The gas administering system of claim 37, further comprising a scavenging device for scavenging gas expired from the mouth of the patient.

44. The gas administering system of claim 37, further comprising a gas flow meter for measuring the gas flow rate of the gas provided by said gas source.

* * * * *